US010190176B2

(12) United States Patent
Madico et al.

(10) Patent No.: US 10,190,176 B2

(45) Date of Patent: Jan. 29, 2019

(54) PRIMERS, PROBES, AND METHODS FOR MYCOBACTERIUM TUBERCULOSIS SPECIFIC DIAGNOSIS

(71) Applicant: BOSTON MEDICAL CENTER CORPORATION, Boston, MA (US)

(72) Inventors: Guillermo E. Madico, Natick, MA (US); Edward C. Jones Lopez, Arlington, MA (US)

(73) Assignee: BOSTON MEDICAL CENTER CORPORATION, Boston, MA (US)

(*) Notice: Subject to any disclaimer, the term of this patent is extended or adjusted under 35 U.S.C. 154(b) by 160 days.

(21) Appl. No.: 14/649,205

(22) PCT Filed: Dec. 4, 2013

(86) PCT No.: PCT/US2013/073164

§ 371 (c)(1),
(2) Date: Jun. 2, 2015

(87) PCT Pub. No.: WO2014/089233

PCT Pub. Date: Jun. 12, 2014

(65) Prior Publication Data

US 2015/0299778 A1 Oct. 22, 2015

Related U.S. Application Data

(60) Provisional application No. 61/733,348, filed on Dec. 4, 2012.

(51) Int. Cl.

*C07K 14/35* (2006.01)
*C12Q 1/689* (2018.01)
*C12Q 1/6883* (2018.01)

(52) U.S. Cl.

CPC .............. *C12Q 1/689* (2013.01); *C07K 14/35* (2013.01); *C12Q 1/6883* (2013.01); *C12Q 2600/156* (2013.01); *C12Q 2600/158* (2013.01)

(58) Field of Classification Search

None

See application file for complete search history.

(56) References Cited

U.S. PATENT DOCUMENTS

| | | | | |
|---|---|---|---|---|
| 6,294,328 | B1 * | 9/2001 | Fleischmann | C12Q 1/689 435/6.15 |
| 7,026,467 | B2 * | 4/2006 | Keim | C12Q 1/689 424/184.1 |
| 7,332,597 | B2 | 2/2008 | Lele | |
| 7,592,135 | B2 * | 9/2009 | Keim | C12Q 1/689 424/184.1 |
| 7,867,704 | B2 * | 1/2011 | Kapur | C12Q 1/689 435/243 |
| 8,263,330 | B1 | 9/2012 | Exner | |
| 8,541,208 | B1 * | 9/2013 | Plesch | C07K 14/245 435/106 |
| 2002/0164588 | A1 * | 11/2002 | Eisenberg | G06F 19/18 435/6.16 |
| 2004/0029129 | A1 * | 2/2004 | Wang | C07K 14/195 435/6.18 |
| 2005/0266492 | A1 * | 12/2005 | Keim | C12Q 1/689 435/6.11 |
| 2006/0046253 | A1 | 3/2006 | Nakao | |
| 2008/0085284 | A1 * | 4/2008 | Patell | C12Q 1/689 424/184.1 |
| 2012/0100545 | A1 | 4/2012 | Inoue | |
| 2015/0299778 | A1 * | 10/2015 | Madico | C07K 14/35 514/254.11 |

FOREIGN PATENT DOCUMENTS

| | | | | |
|---|---|---|---|---|
| WO | 93/22330 | A1 | 11/1993 | |
| WO | 2004/009837 | A2 | 1/2004 | |
| WO | WO-2004009837 | A2 * | 1/2004 | C12Q 1/689 |
| WO | 2011/002418 | A1 | 1/2011 | |
| WO | 2011/140237 | A2 | 11/2011 | |
| WO | WO-2014089233 | A2 * | 6/2014 | C07K 14/35 |

OTHER PUBLICATIONS

Madico et al, PLoS One, Jul. 7, 2016, 11/7:e0158373, 15 pages.*
Triccas et al, Immunology and Cell Biology, 2000, 78:311-317.*
Graham, James E., et al., "Identification of Mycobacterium tuberculosis RNAs synthesized in response of phagocytosis by human macrophages by selective capture of transcribed sequences (SCOTS)," Proc. Natl. Acad. Sci. USA, vol. 96, pp. 11554-11559 (1999).
Cepheid Xpert MTB/RIF Product Page, Nov. 30, 2012.

* cited by examiner

*Primary Examiner* — Nita M. Minnifield

(74) *Attorney, Agent, or Firm* — Arrigo, Lee, Guttman & Mouta-Bellum LLP

(57) ABSTRACT

This invention pertains to probes, primers and associated methods suitable for the analysis and diagnosis of *Mycobacterium tuberculosis*, among other things.

14 Claims, 11 Drawing Sheets

Specification includes a Sequence Listing.

Sequence Alignment

```
    1            3-ponA-F →                                                                              100
MTB AGCTGACCGT TGCCGAAGGG GCGTTGTTGG CAGCGCTGAT TCGGCGGCCT TCGACGCTGG ACCCGGCGGT CGACCCCGAA GGGGCCCATG CCCGCTGGAA
MKA ....C..... GT....G..T ......C... .G.....T.. CA....A..G ..C....... .......... ......G... ..T..AGTC. .G..G.....
MAV ....C..... GT....G..T ...C..C... .G........ C..C.....G ..C..C.... .......C.. ...T...A.G ..C..G.TG. .G........
NOC .......... G.....G..C ...G..C.C. .G..CACT.. C.A..T...G ...G..T... .T....A.CA GA.......G ..C...A.G. ..........

    101                          3-ponA-probe                            ← 3-ponA-R                          200
MTB TTGGGTACTC GACGGCATGG TGGAAACCAA GGCTCTCTCG CCGAATGACC GTGCGGCGCA GGTGTTTCCC GAGACAGTGC CGCCCGATCT GGCCCGGGCA
MKA C.....G... .......... .C..G..... ...C..G..C G.CC.G.... .G..T.AA.. .CA...C... A....C..C. ....G..G.A ......C..G
MAV C.....G... .......... ....G..... ...G..GC.C G.C..G.... ....C..... ...C..C..G C....C.... .......C.A ...G..C..G
NOC C.AC..G... .......... ..TCGGAGGG CAA...GC.C G.CGCC..A. .CAA.T..AT .CA..AC..G .C.GTGCGT. ...TG.CCTC .CT.G.C.AC
```

MTB = *M. tuberculosis*, MKA = *M. kansasii*, MAV = *M. avium*, NOC = *Nocardia* sp.

*FIG. 1A*

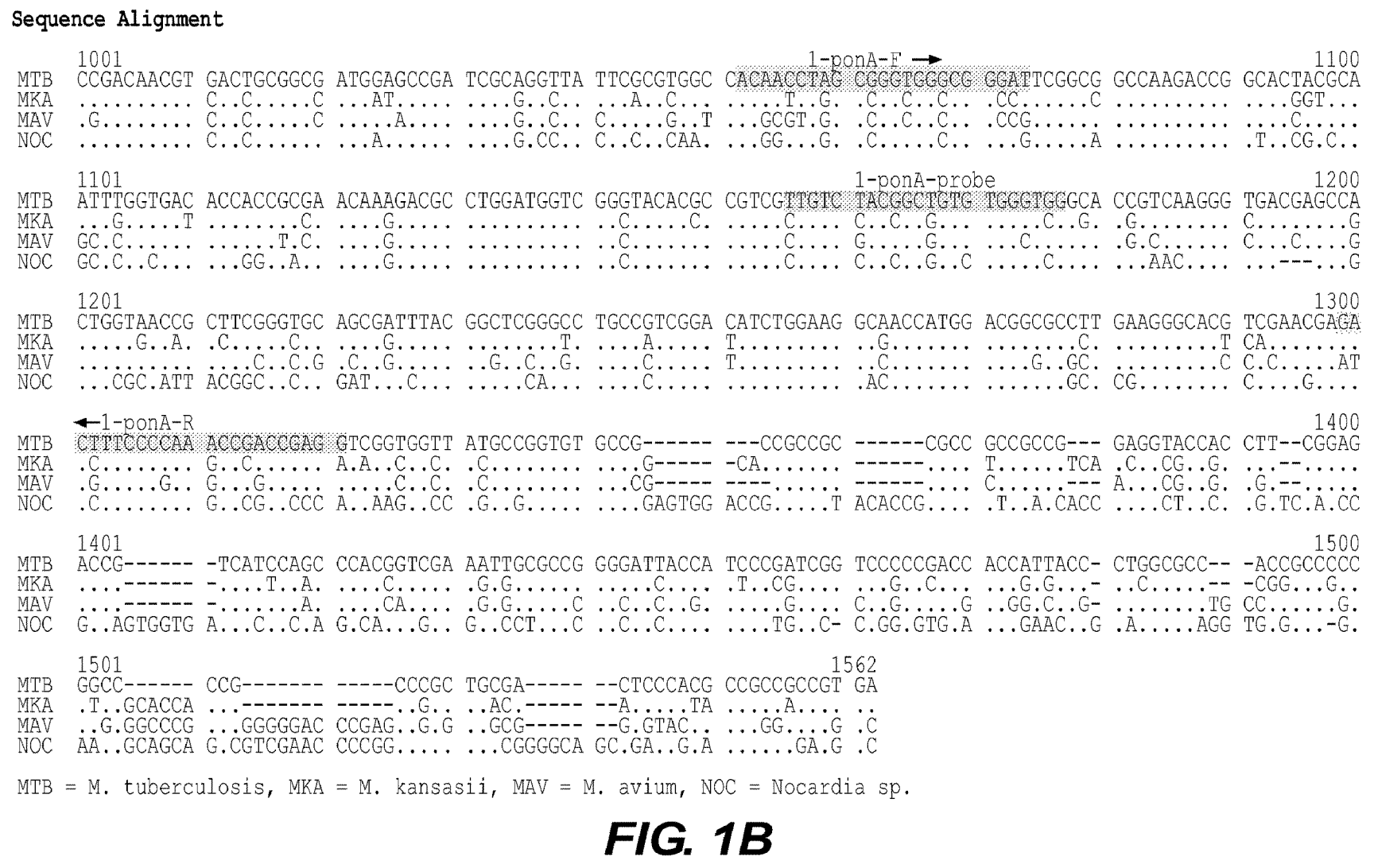

Sequence Alignment

```
                                                         1-ponA-F →
     1001                                                                                                      1100
MTB  CCGACAACGT GACTGCGGCG ATGGAGCCGA TCGCAGGTTA TTCGCGTGGC CACAACCTAG CGGGTGGGCG GGATTCGGCG GCCAAGACCG GCACTACGCA
MKA  .......... C..C.....C ...AT..... ....G..C.. ...A..C... .....T..G. .C..C..C.. .CC......C .......... ....GGT...
MAV  .G........ C..C.....C .....A.... ....G..C.. C.....G..T ...GCGT.G. .C..C..C.. .CCG...... .......... ....C.....
NOC  .......... C..C...... ...A...... ....G.CC.. C..C..CAA. ...GG...G. .C.....C.. ...G.....A .......... .T..CG.C..

                                                                    1-ponA-probe
     1101                                                                                                      1200
MTB  ATTTGGTGAC ACCACCGCGA ACAAAGACGC CTGGATGGTC GGGTACACGC CGTCGTTGTC TACGGCTGTG TGGGTGGGCA CCGTCAAGGG TGACGAGCCA
MKA  ...G.....T ........C. ....G..... .......... ..C.....C. .....C.... C..C..G... .....C..G. .G........ C........G
MAV  GC.C...... ......T.C. ....G..... .......... ..C....... .....C.... G.....G... ...C...... .G.C...... C...C....G
NOC  GC.C..C... ...GG..A.. ....G..... .......... ..C....... .....C.... C..C..G..C .....C.... ...AAC.... ...---...G

     1201                                                                                                      1300
MTB  CTGGTAACCG CTTCGGGTGC AGCGATTTAC GGCTCGGGCC TGCCGTCGGA CATCTGGAAG GCAACCATGG ACGGCGCCTT GAAGGGCACG TCGAACGAGA
MKA  .....G..A. .C.....C.. ....G..... ........T. ....A..... T......... ..G....... ........C. .........T CA........
MAV  .......... ....C..C.G .C..G..... ..G..C..G. ....C..... T......... ..C....... ....G..GC. .........C C.C.....AT
NOC  ...CGC.ATT ACGGC..C.. GAT...C... .....CA... ....C..... .......... .AC....... .......GC. CG........ C....G....

     ← 1-ponA-R                                                                                                1400
MTB  CTTTCCCCAA ACCGACCGAG GTCGGTGGTT ATGCCGGTGT GCCG------ ---CCGCCGC ------CGCC GCCGCCG--- GAGGTACCAC CTT--CGGAG
MKA  .C........ G..C...... A.A..C..C. .C........ ....G----- -CA....... ------.... T......TCA .C..CG..G. ...--.....
MAV  .G.....G.. G...G..... .....C..C. .C........ ...CG----- ----...... ------.... C......--- A...CG..G. .G.--.....
NOC  .C........ G..CG..CCC A..AAG..CC .G..G..... ....GAGTGG ACCG.....T ACACCG.... .T..A.CACC ....CT..C. .G.TC.A.CC

     1401                                                                                                      1500
MTB  ACCG------ -TCATCCAGC CCACGGTCGA AATTGCGCCG GGGATTACCA TCCCGATCGG TCCCCCGACC ACCATTACC- CTGGCGCC-- -ACCGCCCCC
MKA  ....------ -....T..A. ....C..... .G.G...... .....C.... .T..CG.... ...G..C... ...G.G...- ..C.....-- -CGG...G..
MAV  ....------ -.......A. ....CA.... .G.G.....C ..C..C..G. .....G.... C..G.....G ..GG.C..G- ........TG CC......G.
NOC  G..AGTGGTG A...C..C.A G.CA...G.. G..CCT...C ..C..C.... ....TG..C- C.GG.GTG.A ...GAAC..G .A.....AGG TG.G...-G.

     1501                                                           1562
MTB  GGCC------ CCG------- -----CCCGC TGCGA----- --CTCCCACG CCGCCGCCGT GA
MKA  .T..GCACCA ...------- -----..G.. ..AC.----- --A.....TA .....A.... ..
MAV  ..G.GGCCCG ...GGGGGAC CCGAG..G.G ..GCG----- --G.GTAC.. ...GG....G .C
NOC  AA..GCAGCA G.CGTCGAAC CCCGG..... ...CGGGGCA GC.GA..G.A ......GA.G .C
```

MTB = M. tuberculosis, MKA = M. kansasii, MAV = M. avium, NOC = Nocardia sp.

*FIG. 1B*

Sequence Alignment

```
    1001                                                                                                       1100
MTB CCGACAACGT GACTGCGGCG ATGGAGCCGA TCGCAGGTTA TTCGCGTGGC CACAACCTAG CGGGTGGGCG GGATTCGGCG GCCAAGACCG GCACTACGCA
MKA .......... C..C.....C ...AT..... ....G..C.. ...A..C... .....T..G. .C..C..C.. .CC......C .......... ....GGT...
MAV .G........ C..C.....C .....A.... ....G..C.. C.....G..T ...GCGT.G. .C..C..C.. .CCG...... .......... ....C.....
NOC .......... C..C...... ...A...... ....G.CC.. C..C..CAA. ...GG...G. .C.....C.. ...G.....A .......... .T..CG.C..

    1101                                                                                                       1200
MTB ATTTGGTGAC ACCACCGCGA ACAAAGACGC CTGGATGGTC GGGTACACGC CGTCGTTGTC TACGGCTGTG TGGGTGGGCA CCGTCAAGGG TGACGAGCCA
MKA ...G.....T ........C. ....G..... .......... ..C.....C. .....C.... C..C..G... .....C..G. .G........ C........G
MAV GC.C...... ......T.C. ....G..... .......... ..C....... .....C.... G.....G... ...C...... .G.C...... C...C....G
NOC GC.C..C... ...GG..A.. ....G..... .......... ..C....... .....C.... C..C..G..C .....C.... ...AAC.... ...---...G

    1201                                                                                                       1300
MTB CTGGTAACCG CTTCGGGTGC AGCGATTTAC GGCTCGGGCC TGCCGTCGGA CATCTGGAAG GCAACCATGG ACGGCGCCTT GAAGGGCACG TCGAACGAGA
MKA .....G..A. .C.....C.. ....G..... ........T. ....A..... T......... ..G....... ........C. .........T CA........
MAV .......... ....C..C.G .C..G..... ..G..C..G. ....C..... T......... ..C....... ....G..GC. .........C C.C.....AT
NOC ...CGC.ATT ACGGC..C.. GAT...C... .....CA... ....C..... .......... .AC....... .......GC. CG........ C....G....

     2-ponA-F →                                                                                                1400
MTB CTTTCCCCAA ACCGACCGAG GTCGGTGGTT ATGCCGGTGT GCCG------ ---CCGCCGC ------CGCC GCCGCCG--- GAGGTACCAC CTT--CGGAG
MKA .C........ G..C...... A.A..C..C. .C........ ....G----- -CA....... ------.... T......TCA .C..CG..G. ...--.....
MAV .G.....G.. G...G..... .....C..C. .C........ ...CG----- ----...... ------.... C......--- A...CG..G. .G.--.....
NOC .C........ G..CG..CCC A..AAG..CC .G..G..... ....GAGTGG ACCG.....T ACACCG.... .T..A.CACC ....CT..C. .G.TC.A.CC

    1401                                                                          2-ponA-probe                 1500
MTB ACCG------ -TCATCCAGC CCACGGTCGA AATTGCGCCG GGGATTACCA TCCCGATCGG TCCCCCGACC ACCATTACC- CTGGCGCC-- -ACCGCCCCC
MKA ....------ -....T..A. ....C..... .G.G...... .....C.... .T..CG.... ...G..C... ...G.G...- ..C.....-- -CGG...G..
MAV ....------ -.......A. ....CA.... .G.G.....C ..C..C..G. .....G.... C..G.....G ..GG.C..G- ........TG CC......G.
NOC G..AGTGGTG A...C..C.A G.CA...G.. G..CCT...C ..C..C.... ....TG..C- C.GG.GTG.A ...GAAC..G .A.....AGG TG.G...-G.

    1501                                      ← 2-ponA-R            1562
MTB GGCC------ CCG------- -----CCCGC TGCGA----- --CTCCCACG CCGCCGCCGT GA
MKA .T..GCACCA ...------- -----..G.. ..AC.----- --A.....TA .....A.... ..
MAV ..G.GGCCCG ...GGGGGAC CCGAG..G.G ..GCG----- --G.GTAC.. ...GG....G .C
NOC AA..GCAGCA G.CGTCGAAC CCCGG..... ...CGGGGCA GC.GA..G.A ......GA.G .C
```

MTB = *M. tuberculosis*, MKA = *M. kansasii*, MAV = *M. avium*, NOC = *Nocardia* sp.

FIG. 1C

Sequence Alignment

```
     1001                                                        1-ponA-F →                                  1100
MTB  CCGACAACGT GACTGCGGCG ATGGAGCCGA TCGCAGGTTA TTCGCGTGGC CACAACCTAG CGGGTGGGCG GCATTCGGCG GCCAAGACCG GCACTACGCA
MKA  .......... C..C.....C ...AT..... ....G..C.. ...A..C... .....T..G. .C..C..C.. .CC......C .......... ....GGT...
MAV  .G........ C..C.....C .....A.... ....G..C.. C.....G..T ...GCGT.G. .C..C..C.. .CCG...... .......... ....C.....
NOC  .......... C..C...... ...A...... ....G.CC.. C..C..CAA. ...GG...G. .C.....C.. ...G.....A .......... .T..CG.C..

     1101                                                     1-ponA-probe-a                                 1200
MTB  ATTTGGTGAC ACCACCGCGA ACAAAGACGC CTGGATGGTC GGGTACACGC CGTCGTTGTC TACGGCTGTG TGGGTGGGCA CCGTCAAGGG TGACGAGCCA
MKA  ...G.....T ........C. ....G..... .......... ..C.....C. .....C.... C..C..G... .....C..G. .G........ C........G
MAV  GC.C...... ......T.C. ....G..... .......... ..C....... .....C.... G.....G... ...C...... .G.C...... C...C....G
NOC  GC.C..C... ...GG..A.. ....G..... .......... ..C....... .....C.... C..C..G..C .....C.... ...AAC.... ...---...G

     1201                                                                                                    1300
MTB  CTGGTAACCG CTTCGGGTGC AGCGATTTAC GGCTCGGGCC TGCCGTCGGA CATCTGGAAG GCAACCATGG ACGGCGCCTT GAAGGGCACG TCGAACGAGA
MKA  .....G..A. .C.....C.. ....G..... ........T. ....A..... T......... ..G....... ........C. .........T CA........
MAV  .......... ....C..C.G .C..G..... ..G..C..G. ....C..... T......... ..C....... ....G..GC. .........C C.C.....AT
NOC  ...CGC.ATT ACGGC..C.. GAT...C... .....CA... ....C..... .......... .AC....... .......GC. CG........ C....G....

    ← 1-ponA-R                                                                                               1400
MTB  CTTTCCCCAA ACCGACCGAG GTCGGTGGTT ATGCCGGTGT GCCG------ ---CCGCCGC ------CGCC GCCGCCG--- GAGGTACCAC CTT--CGGAG
MKA  .C........ G..C...... A.A..C..C. .C........ ....G----- -CA....... ------.... T......TCA .C..CG..G. ...--.....
MAV  .G.....G.. G...G..... .....C..C. .C........ ...CG----- ----...... ------.... C......--- A...CG..G. .G.--.....
NOC  .C........ G..CG..CCC A..AAG..CC .G..G..... ....GAGTGG ACCG.....T ACACCG.... .T..A.CACC ....CT..C. .G.TC.A.CC

     1401                                                                                                    1500
MTB  ACCG------ -TCATCCAGC CCACGGTCGA AATTGCGCCG GGGATTACCA TCCCGATCGG TCCCCCGACC ACCATTACC- CTGGCGCC-- -ACCGCCCCC
MKA  ....------ -....T..A. ....C..... .G.G...... .....C.... .T..CG.... ...G..C... ...G.G...- ..C.....-- -CGG...G..
MAV  ....------ -.......A. ....CA.... .G.G.....C ..C..C..G. .....G.... C..G.....G ..GG.C..G- ........TG CC......G.
NOC  G..AGTGGTG A...C..C.A G.CA...G.. G..CCT...C ..C..C.... ....TG..C- C.GG.GTG.A ...GAAC..G .A.....AGG TG.G...-G.
```

MTB = *M. tuberculosis*, MKA = *M. kansasii*, MAV = *M. avium*, NOC = *Nocardia* sp.

FIG. 1D

MTB = *M. tuberculosis*, MKA = *M. kansasii*, MAV = *M. avium*, NOC = *Nocardia* sp.

SEQUENCE LISTING

```
<160> NUMBER OF SEQ ID NOS: 50

<210> SEQ ID NO 1
<211> LENGTH: 28
<212> TYPE: DNA
<213> ORGANISM: Mycobacterium tuberculosis

<400> SEQUENCE: 1

tgaccgttgc cgaaggggcg ttgttggc                                        28


<210> SEQ ID NO 2
<211> LENGTH: 28
<212> TYPE: DNA
<213> ORGANISM: Mycobacterium tuberculosis

<400> SEQUENCE: 2

gccaacaacg ccccttcggc aacggtca                                        28


<210> SEQ ID NO 3
<211> LENGTH: 25
<212> TYPE: DNA
<213> ORGANISM: Mycobacterium tuberculosis

<400> SEQUENCE: 3

tttcccgaga cagtgccgcc cgatc                                           25
```

<210> SEQ ID NO 4
<211> LENGTH: 25
<212> TYPE: DNA
<213> ORGANISM: Mycobacterium tuberculosis

<400> SEQUENCE: 4
gatcgggcgg cactgtctcg ggaaa 25

<210> SEQ ID NO 5
<211> LENGTH: 25
<212> TYPE: DNA
<213> ORGANISM: Mycobacterium tuberculosis

<400> SEQUENCE: 5
cacaacctag cgggtgggcg ggatt 25

<210> SEQ ID NO 6
<211> LENGTH: 25
<212> TYPE: DNA
<213> ORGANISM: Mycobacterium tuberculosis

<400> SEQUENCE: 6
aatcccgccc acccgctagg ttgtg 25

<210> SEQ ID NO 7
<211> LENGTH: 25
<212> TYPE: DNA
<213> ORGANISM: Mycobacterium tuberculosis

<400> SEQUENCE: 7
agactttccc caaaccgacc gaggt 25

<210> SEQ ID NO 8
<211> LENGTH: 25
<212> TYPE: DNA
<213> ORGANISM: Mycobacterium tuberculosis

<400> SEQUENCE: 8
acctcggtcg gtttggggaa agtct 25

<210> SEQ ID NO 9
<211> LENGTH: 22
<212> TYPE: DNA
<213> ORGANISM: Mycobacterium tuberculosis

<400> SEQUENCE: 9
gcgactccca cgccgccgcc gt 22

<210> SEQ ID NO 10
<211> LENGTH: 22
<212> TYPE: DNA
<213> ORGANISM: Mycobacterium tuberculosis

<400> SEQUENCE: 10
acggcggcgg cgtgggagtc gc 22

<210> SEQ ID NO 11
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 11
gaccgttacc gaaggggcgt tgttgg 26

<210> SEQ ID NO 12
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 12
ccaacaacgc cccttcggta acggtc 26

<210> SEQ ID NO 13
<211> LENGTH: 23
<212> TYPE: DNA
<213> ORGANISM: Mycobacterium tuberculosis

<400> SEQUENCE: 13
ttcccgagac agtgccgccc gat 23

<210> SEQ ID NO 14
<211> LENGTH: 23
<212> TYPE: DNA
<213> ORGANISM: Mycobacterium tuberculosis

<400> SEQUENCE: 14
atcgggcggc actgtctcgg gaa 23

<210> SEQ ID NO 15
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 15
acaacatagc gggtgggcgg gat 23

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
atcccgccca cccgctatgt tgt 23

<210> SEQ ID NO 17
<211> LENGTH: 23
<212> TYPE: DNA
<213> ORGANISM: Mycobacterium tuberculosis

<400> SEQUENCE: 17
gactttcccc aaaccgaccg agg 23

<210> SEQ ID NO 18
<211> LENGTH: 23
<212> TYPE: DNA
<213> ORGANISM: Mycobacterium tuberculosis

<400> SEQUENCE: 18
cctcggtcgg tttggggaaa gtc 23

<210> SEQ ID NO 19
<211> LENGTH: 20
<212> TYPE: DNA
<213> ORGANISM: Mycobacterium tuberculosis

<400> SEQUENCE: 19
cgactcccac gccgccgccg 20

<210> SEQ ID NO 20
<211> LENGTH: 20
<212> TYPE: DNA
<213> ORGANISM: Mycobacterium tuberculosis

<400> SEQUENCE: 20
cggcggcggc gtgggagtcg 20

<210> SEQ ID NO 21
<211> LENGTH: 27
<212> TYPE: DNA
<213> ORGANISM: Mycobacterium tuberculosis

<400> SEQUENCE: 21
aaaccaaggc tctctcgccg aatgacc 27

<210> SEQ ID NO 22
<211> LENGTH: 27
<212> TYPE: DNA
<213> ORGANISM: Mycobacterium tuberculosis

<400> SEQUENCE: 22
ggtcattcgg cgagagagcc ttggttt 27

<210> SEQ ID NO 23
<211> LENGTH: 24
<212> TYPE: DNA
<213> ORGANISM: Mycobacterium tuberculosis

<400> SEQUENCE: 23
gttgtctacg gctgtgtggg tggg 24

<210> SEQ ID NO 24
<211> LENGTH: 24
<212> TYPE: DNA
<213> ORGANISM: Mycobacterium tuberculosis

<400> SEQUENCE: 24
cccacccaca cagccgtaga caac 24

<210> SEQ ID NO 25
<211> LENGTH: 25
<212> TYPE: DNA
<213> ORGANISM: Mycobacterium tuberculosis

<400> SEQUENCE: 25
ggtcccccga ccaccattac cctgg 25

<210> SEQ ID NO 26
<211> LENGTH: 25
<212> TYPE: DNA
<213> ORGANISM: Mycobacterium tuberculosis

<400> SEQUENCE: 26

-continued ccagggtaat ggtggtcggg ggacc 25

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 27
aaccaaggct ctctcaccga atgac 25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28
gtcattcggt gagagagcct tggtt 25

<210> SEQ ID NO 29
<211> LENGTH: 22
<212> TYPE: DNA
<213> ORGANISM: Mycobacterium tuberculosis

<400> SEQUENCE: 29
ttgtctacgg ctgtgtgggt gg 22

<210> SEQ ID NO 30
<211> LENGTH: 22
<212> TYPE: DNA
<213> ORGANISM: Mycobacterium tuberculosis

<400> SEQUENCE: 30
ccacccacac agccgtagac aa 22

<210> SEQ ID NO 31
<211> LENGTH: 23
<212> TYPE: DNA
<213> ORGANISM: Mycobacterium tuberculosis

<400> SEQUENCE: 31
gtcccccgac caccattacc ctg 23

<210> SEQ ID NO 32
<211> LENGTH: 23
<212> TYPE: DNA
<213> ORGANISM: Mycobacterium tuberculosis

<400> SEQUENCE: 32
cagggtaatg gtggtcgggg gac 23

<210> SEQ ID NO 33
<211> LENGTH: 24
<212> TYPE: DNA
<213> ORGANISM: Mycobacterium tuberculosis

<400> SEQUENCE: 33
gtcccccgac caccattacc ctgg 24

<210> SEQ ID NO 34
<211> LENGTH: 24

-continued

<212> TYPE: DNA
<213> ORGANISM: Mycobacterium tuberculosis

<400> SEQUENCE: 34
ccagggtaat ggtggtcggg ggac 24

<210> SEQ ID NO 35
<211> LENGTH: 22
<212> TYPE: DNA
<213> ORGANISM: Mycobacterium tuberculosis

<400> SEQUENCE: 35
tcccccgacc accattaccc tg 22

<210> SEQ ID NO 36
<211> LENGTH: 22
<212> TYPE: DNA
<213> ORGANISM: Mycobacterium tuberculosis

<400> SEQUENCE: 36
cagggtaatg gtggtcgggg ga 22

<210> SEQ ID NO 37
<211> LENGTH: 25
<212> TYPE: DNA
<213> ORGANISM: Mycobacterium tuberculosis

<400> SEQUENCE: 37
ccgtcgttgt ctacggctgt gtggg 25

<210> SEQ ID NO 38
<211> LENGTH: 25
<212> TYPE: DNA
<213> ORGANISM: Mycobacterium tuberculosis

<400> SEQUENCE: 38
cccacacagc cgtagacaac gacgg 25

<210> SEQ ID NO 39
<211> LENGTH: 26
<212> TYPE: DNA
<213> ORGANISM: Mycobacterium tuberculosis

<400> SEQUENCE: 39
aggtcggtgg ttatgccggt gtgccg 26

<210> SEQ ID NO 40
<211> LENGTH: 26
<212> TYPE: DNA
<213> ORGANISM: Mycobacterium tuberculosis

<400> SEQUENCE: 40
cggcacaccg gcataaccac cgacct 26

<210> SEQ ID NO 41
<211> LENGTH: 23
<212> TYPE: DNA
<213> ORGANISM: Mycobacterium tuberculosis

<400> SEQUENCE: 41
cgtcgttgtc tacggctgtg tgg 23

<210> SEQ ID NO 42

<211> LENGTH: 23
<212> TYPE: DNA
<213> ORGANISM: Mycobacterium tuberculosis

<400> SEQUENCE: 42
ccacacagcc gtagacaacg acg 23

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 43
ggtcggtggt tatgcgggtg tgcc 24

<210> SEQ ID NO 44
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 44
ggcacacccg cataaccacc gacc 24

<210> SEQ ID NO 45
<211> LENGTH: 17
<212> TYPE: DNA
<213> ORGANISM: Mycobacterium tuberculosis

<400> SEQUENCE: 45
ggccggtggt cgccgcg 17

<210> SEQ ID NO 46
<211> LENGTH: 19
<212> TYPE: DNA
<213> ORGANISM: Mycobacterium tuberculosis

<400> SEQUENCE: 46
acgtgacaga ccgccgggc 19

<210> SEQ ID NO 47
<211> LENGTH: 1505
<212> TYPE: DNA
<213> ORGANISM: Mycobacterium tuberculosis

<400> SEQUENCE: 47
agctgaccgt tgccgaaggg gcgttgttgg cagcgctgat tcggcggcct tcgacgctgg 60
acccggcggt cgaccccgaa ggggcccatg cccgctggaa ttgggtactc gacggcatgg 120
tggaaaccaa ggctctctcg ccgaatgacc gtgcggcgca ggtgtttccc gagacagtgc 180
cgcccgatct ggcccgggca gagaatcaga ccaaaggacc caacgggctg atcgagcggc 240
aggtgacaag ggagttgctc gagctgttca acatcgacga gcagaccctc aacacccagg 300
ggctggtggt caccaccacg attgatccgc aggcccaacg ggcggcggag aaggcggttg 360
cgaaatacct ggacgggcag gaccccgaca tgcgtgccgc cgtggtttcc atcgacccgc 420
acaacggggc ggtgcgtgcg tactacggtg gcgacaatgc caatggcttt gacttcgctc 480
aagcgggatt gcagactgga tcgtcgttta aggtgtttgc tctggtggcc gcccttgagc 540
aggggatcgg cctgggctac caggtagaca gctctccgtt gacggtcgac ggcatcaaga 600

-continued tcaccaacgt cgagggcgag ggttgcggga cgtgcaacat cgccgaggcg ctcaaaatgt 660
cgctgaacac ctcctactac cggctgatgc tcaagctcaa cggcggccca caggctgtgg 720
ccgatgccgc gcaccaagcc ggcattgcct ccagcttccc gggcgttgcg cacacgctgt 780
ccgaagatgg caagggtgga ccgcccaaca acgggatcgt gttgggccag taccaaaccc 840
gggtgatcga catggcatcg gcgtatgcca cgttggccgc gtccggtatc taccacccgc 900
cgcatttcgt acagaaggtg gtcagtgcca acggccaggt cctcttcgac gccagcaccg 960
cggacaacac cggcgatcag cgcatcccca aggcggtagc cgacaacgtg actgcggcga 1020
tggagccgat cgcaggttat tcgcgtggcc acaacctagc gggtgggcgg gattcggcgg 1080
ccaagaccgg cactacgcaa tttggtgaca ccaccgcgaa caaagacgcc tggatggtcg 1140
ggtacacgcc gtcgttgtct acggctgtgt gggtgggcac cgtcaagggt gacgagccac 1200
tggtaaccgc ttcgggtgca gcgatttacg gctcgggcct gccgtcggac atctggaagg 1260
caaccatgga cggcgccttg aagggcacgt cgaacgagac tttccccaaa ccgaccgagg 1320
tcggtggtta tgccggtgtg ccgccgccgc cgccgccgcc ggaggtacca ccttcggaga 1380
ccgtcatcca gcccacggtc gaaattgcgc cggggattac catcccgatc ggtcccccga 1440
ccaccattac cctggcgcca ccgcccccgg ccccgcccgc tgcgactccc acgccgccgc 1500
cgtga 1505

<210> SEQ ID NO 48
<211> LENGTH: 1526
<212> TYPE: DNA
<213> ORGANISM: Mycobacterium avium

<400> SEQUENCE: 48
agctcaccgt gtccgagggt gcgctgctgg cggcgctgat ccgccggccg tccaccctgg 60
acccggccgt cgatcccaag ggcgcgctgg cgcgctggaa ctgggtgctc gacggcatgg 120
tggagaccaa ggcgctgccc gccaaggacc gtgccgcgca ggtcttcccg cagaccgtgc 180
cgcccgacca ggcgcgcgcg cagaaccaga cgaccgggcc caacggcctg atcgagcgtc 240
aggtgaccaa ggagctgatg gagctcttca acatcgacga gcggacgctg aacacgcagg 300
gcctgcaggt caccaccacc atcgacccca aggcccagca ggccgccgag aaggcggtgt 360
cgaaatacct tgacgggcaa gaccccgaca tgcgcgcggc ggtggtgtcg gtggatccgc 420
acgacggcgc catccgcgcc tactacggcg gtagcgacgc caacggtttc gacttcgccc 480
aggcgggatt gcagaccggc tcgtcgttca aggtgttctg cctgatcgcc gcgcttgagc 540
agggcatcgg cctgggctac caggtggaca gctcgccgct gacggtcgac ggcatcaaga 600
tcaccaacgt cgagggcgag agctgcggga cgtgcaacat cgcgcaggcg ctcaagatgt 660
cgttgaacac ctcctattac cggctgatgc tcaaactcaa gggcgggccg caggccgtgg 720
ccgatgccgc gcatcaggca ggcgttgcca cgagttttcc cggcgtggac cacacgctgt 780
ccgaggacgg caagggcggg ccgccgaaca acggaattgt gctgggccag taccaaaccc 840
gggtgatcga catggcctcg gcgtacgcca cgctggccgc ctcgggcgtc taccaccggc 900
cgcatttcgt gcagaaggtg gtcaactcgg acggtcaggt gctcttcgac gccggcaagt 960
ccgacaacaa cggcgagcag cggatcccga aggccgtcgc ggacaacgtc accgcggcca 1020
tggaaccgat cgcgggctac tcgcggggtc acgcgttggc cggcggccgg ccgtcggcgg 1080
ccaagaccgg caccacgcag ctcggtgaca ccacctccaa caaggacgcc tggatggtcg 1140
gctacacgcc gtcgctgtcg acggcggtgt ggctgggcac ggccaagggc gaccagccgc 1200
tggtaaccgc ttccggcgga ccggtttacg ggtccgggct gccctcggat atctggaagg 1260
ccaccatgga cggggcgctg aagggcaccc ccaacgaatc gttcccgaag ccggccgagg 1320
tcggcggcta cgccggtgtg cccgcgccgc cgcccccgcc gaaggcgccg ccgtcggaga 1380
ccgtcatcca acccaccatc gaagtggcgc ccggcatcac gatcccggtc ggcccgccga 1440
cgacggtcac gctggcgcct gccccgcccg cgggcggccc gccgggggga cccgagccgg 1500
gtggcggtgt accgccgggg ccgggc 1526

<210> SEQ ID NO 49
<211> LENGTH: 1517
<212> TYPE: DNA
<213> ORGANISM: Mycobacterium kansasii

<400> SEQUENCE: 49
agctcaccgt gtccgagggt gcgttgctgg cggcgcttat caggcgaccg tccacgctgg 60
acccggcggt cgacccggaa ggtgcagtcg cgcggtggaa ctgggtgctc gacggcatgg 120
tcgagaccaa ggccctgtcc gcccaggacc gggctgaaca gcagttcccc aagaccgtcc 180
cgccggagca ggcccgcgcg gaaaaccaga ccaccggccc caacggcctg atcgagcgac 240
aggtgaccaa ggaattactg gagctgttca acatcgatga gcagaccctg aacacccagg 300
ggttgcaggt caccaccacg atcgatccgc aagcccagca ggcggccgaa aaggcggtgg 360
ccaagtacct cgacgggcag gatcccgata tgcgggcggc ggtggtgtcc atcgacccgc 420
acaacggagg cgtgcgcgcg tattacggcg gcgacaacgc caacggctac gacttcgccc 480
aggccggatt gcagaccggg tcgtcgttca aggtgttcgc gttggtggcg gccctcgagc 540
aggggatcgg gctgggctat caggtcgaca gttcaccgct aacggtcgac ggcatcaaga 600
tcaccaatgt cgacggcgag ggttgcggga cgtgcaacat cgccgaggcg ctcaagatgt 660
cgctgaacac ctcctattac cggctgatgc tcaaactgaa gggcggcccc caggccgtcg 720
ccgacgccgc ccaccaagcg ggtgtggccg acagtttccc gggcgtaccc cacaccctgt 780
ccgaggatgg caagggcggg ccgccgaaca atgggatcgt gttgggccag taccaaaccc 840
gggtgatcga tatggcaacg gcgtacgcca cgctggccgc gtcgggcatc tatcaccggc 900
cgcacttcgt ccaaaaggta gtcaacgccg aaggccaggt ccttttcgac gccgccaccc 960
aggacgactc cggtgagcag cgcatcccca aagccgtggc cgacaacgtc accgcggcca 1020
tgatgccgat cgcgggctat tcacgcggcc acaatctggc cggcggccgg ccttcggccg 1080
ccaagaccgg cacggtgcaa ttgggtgata ccaccgccaa caaggacgcc tggatggtcg 1140
gctacacccc gtcgctgtcc accgcggtgt gggtcgggac ggtcaagggc gacgagccgc 1200
tggtgacagc ctcgggcgca gcggtttacg gctcgggtct gccatcggat atctggaagg 1260
cgaccatgga cggcgccctg aagggcactc agaacgagac cttccccaag cccaccgaga 1320
taggcggcta cgccggtgtg ccggcaccgc cgccgcctcc gccgtcagcg gcgccgcctt 1380
cggagaccgt cattcaaccc accgtcgaag tggcgccggg gatcaccatt cccgtcggtc 1440
cgcccaccac cgtgaccctc gcgcccgggc cgccgtccgc accaccgccg gctgacaatc 1500
ccataccgcc accgtga 1517

<210> SEQ ID NO 50
<211> LENGTH: 1544
<212> TYPE: DNA
<213> ORGANISM: Nocardia cyriacigeorgica -continued

<400> SEQUENCE: 50

```
agctgaccgt ggccgagggc gcggtgctcg cggccactat ccagctgccg tcggcgttgg     60
atccggagca gaaccccgag ggcgccaagg cccgctggaa ctacgtgctc gacggcatgg    120
tgtcggaggg caatctgccc gccgccgaac gcaagtcgat gcagtacccg gcggtgcgtc    180
cgctggcctc gctcggcgac aaggccaacg acgacggccc cgagggcttg atcaagcagc    240
aggtgctgcg cgagctgtcg gaagcgggca tcagcgagca gcagctcaac accgcgggct    300
tgcagatcac caccaccatc gatccgaagg cgcagcaggc cgcgctcgat gcggtggccg    360
agaacatgca gggcgagccc gagaagctgc gcaccgccgt ggtctcgatc gatccgaaat    420
ccggtgcggt gcgcgcctac tacggcggca aggacggcca gggctacgac ttcgccaacg    480
cgggcttgca gaccggttcg tcgttcaagg tgttcggcct ggcgcagaac ctggagatgg    540
gcatcccgct gtcgcagatg tacgacagct cgccgctcac cgtgcacggc atcaagatca    600
ccaacgtcga gggtgagtcc tgcggcatgt gcaccatcgc cgaggcgctc aagcgttcgc    660
tgaacaccag cttctaccgc atgcagctgg atatgcagaa cggcccgcag aagatcgccg    720
atatggcgca caagctgggc attccggaag agatcccggg cgtcggcaag accctgaccg    780
aaccggacgg ctccggcccg aacaacggca tcgtgctggg ccagtaccag gcgcgagtgc    840
tcgatatggc ttccgcctac gcgactctcg cggcgtcggg cgtctaccac aagccgcact    900
tcgtgcagcg cgtggtgacc gccgacggtg aggtgctgct cgatcgcggt gaggtcgccg    960
gcgagcagcg cgtctcggct gccgtggccg acaacgtcac cgcggcgatg aagccgatcg   1020
cggcctactc ccgcaaccac ggcctggccg gtggccggga gtcggcagcc aagaccggta   1080
ccgcccagct cggcgacacc ggcgagaaca aggacgcctg gatggtcggc tacacgccgt   1140
cgctgtccac cgcggtctgg gtcggcaccg aacagggtga gccgctgcgc aattacggcg   1200
gcgcgatgat ctacggctcc agcctgccct cggacatctg gaaggacacc atggacggcg   1260
cgctcgaggg cacgccgaag gagaccttcc ccaagcccgc ccccatcaag ggccaggcgg   1320
gtgtgccgga gtggaccgcg ccgtacaccg cgccgtcgac caccgaggct cccccgttcc   1380
agccgccagt ggtgatcacc ccgagccagg tggagatcct gcccggcatc accatccctg   1440
tccccggcgt gcaaccgaac ccgcaggcgc aggtgcggcc gcaaccgcag cagccgtcga   1500
accccggccc gctgccgggg cagccgaccg caccgccgga gggc                    1544
```

PRIMERS, PROBES, AND METHODS FOR MYCOBACTERIUM TUBERCULOSIS SPECIFIC DIAGNOSIS

CROSS-REFERENCE TO RELATED APPLICATIONS

This application claims priority to Provisional Application No. 61/733,348, filed Dec. 4, 2012, which is hereby incorporated herein by reference in its entirety.

REFERENCE TO A SEQUENCE LISTING

The instant application contains a Sequence Listing that has been submitted in ASCII format via EFS-Web and is hereby incorporated by reference in its entirety. Said ASCII copy, created on Dec. 2, 2013, is named 1006_005_PCT.txt and is 16,501 bytes in size.

INTRODUCTION

This invention pertains to the field of pathogen determination and diagnosis and more particularly to the determination and diagnosis of *Mycobacterium tuberculosis* such as in human or veterinary samples.

Practical and rapid methods for the diagnosis of *Mycobacterium tuberculosis* (MTB) using the polymerase chain reaction (PCR) have long been sought particularly because of the incidence of human immunodeficiency virus (HIV) co-infection and because standard culture methods are not practical given the long incubation periods needed and the growing prevalence of drug resistant strains. Historically, MTB has remained difficult to diagnose because of: 1) inherent difficulties in specimen collection and preparation; 2) exceptionally high DNA homology of MTB with other Mycobacteria (water-born and soil-born); 3) unusual homology with human genomic DNA; and 4) MTB's low rate of replication. PCR methodology has demonstrated some commercial success. However, the overall sensitivity of, for example, Cepheid's GeneXpert® MTB/RIF leaves room for improvement.

The inventors have determined that the *Mycobacterium tuberculosis* ("*M. tuberculosis*" or "MTB") ponA gene is extremely conserved among all members of the MTB complex. The inventors have further determined that the MTB ponA gene target is evolutionarily distant from all other ponA genes and therefore provides improved assay sensitivity and specificity. The inventors have identified conserved segments of the MTB ponA gene that are useful, among other things, to identify MTB complex members and that may be used to distinguish MTB complex bacteria from non-MTB complex bacteria. Based in part on these findings, the inventors have designed novel synthetic oligonucleotides that are useful in, for example, methods of detecting the MTB ponA gene in a sample, methods of detecting MTB in a sample, and methods of detecting MTB infection in a subject.

Embodiments of the invention are directed to primers and/or probes that are unique to *Mycobacterium tuberculosis* while avoiding other Mycobacteria and related bacteria. The primers and/or probes are useful for accurate quantification of MTB loads in clinical samples in the range of 5,000 to 0.01 copies. This disclosure presents various amplification methods that can be used, inter alia, to determine *Mycobacterium tuberculosis* (MTB) in clinical specimens. Said methods utilize judiciously selected primers and probes that are capable of uniquely detecting MTB while avoiding other Mycobacteria, contaminating bacteria, and human DNA. Said methods are both highly sensitive and specific. Some examples of such judiciously selected probes and primers are illustrated in FIGS. 1A to 1E and the nucleobase sequences of which are summarized in Table 2.

In some embodiments, the amplification protocol (e.g. asymmetric PCR) is based on a 40:1 ratio of the two primers. This produces primarily single stranded DNA products (i.e. amplicons) that can be determined in capture-probe based systems, in real-time or by end-point analysis. However, it is believed that the capture-based approach to the analysis of end-point methodology improves sensitivity. As shown in the Examples (below) the analytical sensitivity achieved in human specimens was, in some cases, 0.5 to 0.01 MTB genomes/PCR; one to two logs lower than most real-time PCR-based assays can obtain.

Unlike many PCR methods that produce double stranded exponential amplification, the asymmetric PCR methodology that produces primarily single stranded DNA products (that result from asymmetric PCR) amplify in a reproducible linear fashion. The methods disclosed herein are flexible and allow for detection of amplicons in a variety of capture-probe detection assays, for example. In some embodiments the assay can be multiplexed to include the detection of MTB drug resistance markers. Unlike Cepheid's commercially available GeneXpert® MTB/RIF that requires special amplification enzymes, costly and complicated probe labeling chemistry, and laser readout to interrogate the exponential amplification in real-time during each PCR cycle, the end-point approach shown in the Examples below measures amplicons in a safe, simple, and inexpensive manner.

BRIEF DESCRIPTION OF DRAWINGS

The skilled artisan will understand that the drawings, described below, are for illustration purposes only. The drawings are not intended to limit the scope of the present teaching in any way.

FIGS. 1A to 1E show a sequence alignment of *Mycobacterium tuberculosis* ponA (MTM ponA, GI 41352722) (SEQ ID NO: 47) with the ponA genes of *M. Kansasii* (MKA, GI:218125396) (SEQ ID NO: 49), *M. avium* (MAV, GI:41400296) (SEQ ID NO: 48) and *Nocardia cyriacigeorgica* (NOC) (SEQ ID NO: 50). FIG. 1A shows the locations of the MTM ponA gene that correspond to the 3-ponA-F and 3-ponA-R primers and the 3-ponA-probe in grey shading. FIG. 1B shows the locations of the MTM ponA gene that correspond to the 1-ponA-F and 1-ponA-R primers and the 1-ponA-probe in grey shading. FIG. 1C shows the locations of the MTM ponA gene that correspond to the 2-ponA-F and 2-ponA-R primers and the 2-ponA-probe in grey shading. FIG. 1D shows the locations of the MTM ponA gene that correspond to the 1-ponA-F and 1-ponA-R primers and the 1-ponA-probe-a in grey shading. FIG. 1E shows the locations of the MTM ponA gene that correspond to the 2-ponA-F and 2-ponA-R-a primers and the 2-ponA-probe-a in grey shading.

DESCRIPTION

Definitions

Figure 1E:
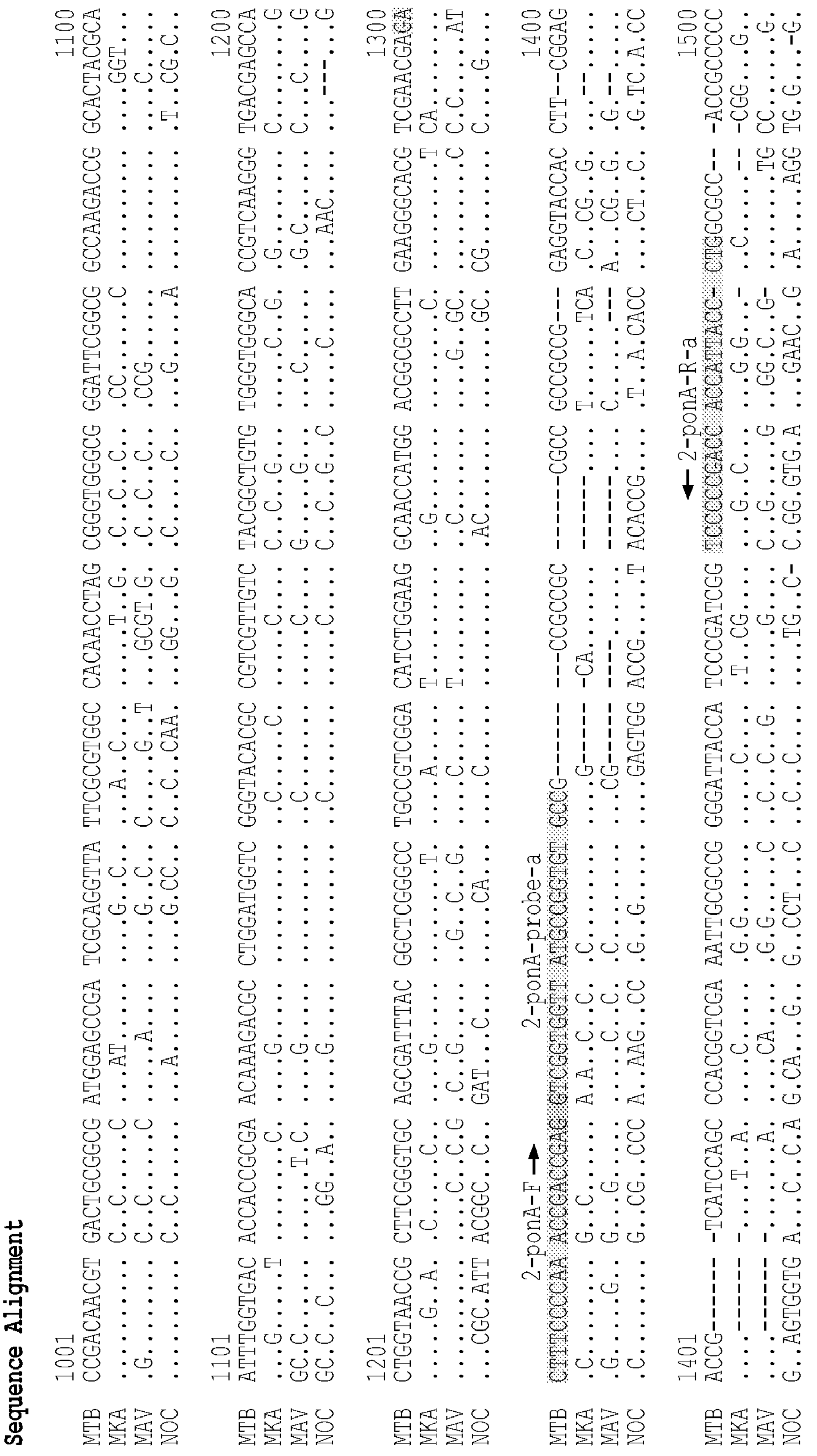

For the purposes of interpreting of this specification, the following definitions will apply and whenever appropriate, terms used in the singular will also include the plural and vice versa. In the event that any definition set forth below conflicts with the usage of that word in any other document, the definition set forth below shall always control for purposes of interpreting the scope and intent of this specification and its associated claims. Notwithstanding the foregoing, the scope and meaning of any document incorporated herein by reference should not be altered by the definition presented below. Rather, said incorporated document should be interpreted as it would be by the ordinary practitioner based on its content and disclosure with reference to the content of the description provided herein.

The use of "or" means "and/or" unless stated otherwise or where the use of "and/or" is clearly inappropriate. The use of "a" means "one or more" unless stated otherwise or where the use of "one or more" is clearly inappropriate. The use of "comprise," "comprises," "comprising" "include," "includes," and "including" are interchangeable and not intended to be limiting. Furthermore, where the description of one or more embodiments uses the term "comprising," those skilled in the art would understand that in some specific instances, the embodiment or embodiments can be alternatively described using language "consisting essentially of" and/or "consisting of."

As used herein "amplicon" refers to DNA or RNA produced as a consequence of the practice of a nucleic acid amplification reaction.

As used herein "calculated binding value" or "GBV" refers to a calculated value based on the actual nucleobase sequence of the probe or primer using the following formula: 1) all cytosine and guanine nucleobases are assigned a value of 3; 2) all adenine, thymine, and uracil nucleobases are assigned a value of 2; and 3) CBVs for each nucleobase sequence are determined by adding each assigned value for the component nucleobases of the nucleobase sequence. For example, the 'calculated binding value' of SEQ ID NO: 6 (a 26-mer oligonucleotide) would be 69; based on the following calculation: G=3, A=2, C=3, C=3, G=3, T=2, T=2, G=3, C=3, C=3, G=3, A=2, A=2, G=3, G=3, G=3, G=3, C=3, G=3, T=2, T=2, G=3, T=2,T=2, G=3, G=3, Total CBV=69.

CBVs of each of SEQ ID NOS: 1-46 are stated below in Table 2; the 'Table of Oligonucleotides'.

As used herein, "nucleic acid" refers to a polynucleobase strand formed from nucleotide subunits composed of a nucleobase, a ribose or 2'-deoxyribose sugar and a phosphate group. Some examples of nucleic acid are DNA and RNA.

As used herein "nucleic acid amplification conditions" refer to conditions used to perform a select nucleic acid amplification process. Nucleic acid amplification is well known in the art. Generally, nucleic acid amplification requires a template, primers, nucleotide triphosphates, magnesium, salts and buffers and a polymerase (or heat stable polymerase). Exact conditions can be determined for each assay using the information provided herein in combination with routine experimentation. Examples of methodologies and the conditions that can be used to practice nucleic acid amplification can be found in: "Nucleic Acid Amplification Technologies: Application to Disease Diagnosis, Lee, Morse and Olsvik, Eaton Publishing, Cambridge, Mass., USA".

As used herein "nucleic acid analog" refers to a polynucleobase strand formed from subunits wherein the subunits comprise a nucleobase and a sugar moiety that is not ribose or 2'-deoxyribose and/or a linkage (between the sugar units) that is not a phosphate group. A non-limiting example of a nucleic acid analog is a locked nucleic acid (LNA: See for example, U.S. Pat. Nos. 6,043,060, 7,053,199, 7,217,805 and 7,427,672). See: Janson and During, "Peptide Nucleic Acids, Morpholinos and Related Antisense Biomolecules", Chapter 7, "Chemistry of Locked Nucleic Acids (LNA)", Springer Science & Business, 2006 for a summary of the chemistry of LNA.

As used herein the phrase "nucleic acid mimic" refers to a nucleobase containing polymer formed from subunits that comprise a nucleobase and a backbone structure that is not a sugar moiety (or that comprises a sugar moiety) but that can nevertheless sequence specifically bind to a nucleic acid. An example of a nucleic acid mimic is peptide nucleic acid (PNA: See for example, U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, WO92/20702 and WO92/20703). Another example of a nucleic acid mimic is a morpholino oligomer. (See Janson and During, "Peptide Nucleic Acids, Morpholinos and Related Antisense Biomolecules", Chapter 6, "Morpholinos and PNAs Compared", Springer Science & Business, 2006 for a discussion of the differences between PNAs and morpholinos.

As used herein "nucleobase" refers to those naturally occurring and those non-naturally occurring heterocyclic moieties commonly used to generate polynucleobase strands that can sequence specifically bind to nucleic acids. Non-limiting examples of nucleobases include: adenine ("A"), cytosine ("C"), guanine ("G"), thymine ("T"), uracil ("U"), 5-propynyl-uracil, 2-thio-5-propynyl-uracil, 5-methylcytosine, pseudoisocytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine).

As used herein "nucleobase sequence" refers to any nucleobase containing segment of a polynucleobase strand (e.g. a subsection of a polynucleobase strand). Non-limiting examples of suitable polynucleobase strands include oligodeoxynucleotides (e.g. DNA), oligoribonucleotides (e.g. RNA), peptide nucleic acids (PNA), PNA chimeras, nucleic acid analogs and/or nucleic acid mimics.

As used herein "nucleobase containing subunit" refers to a subunit of a polynucleobase strand that comprises a nucleobase. For oligonucleotides, the nucleobase containing subunit is a nucleotide. For other types of polynucleobase strands (e.g. nucleic acid analogs), the nucleobase containing subunit will be determined by the nature of the nucleobase containing subunits that make up said polynucleobase strand (i.e. a polynucleobase polymer).

As used herein "point mutation" refers to a single nucleobase substitution (e.g. substitution of an A, C or G for a T) as compared with the original or native nucleobase sequence that forms the basis for the comparison. The term 'point mutation' also includes an insertion or a deletion of a single nucleobase as compared to said original or native nucleobase sequence.

As used herein "polynucleobase strand" refers to a complete single polymer strand comprising nucleobase containing subunits.

As used herein "primer" refers to a polynucleobase strand that binds to a select target sequence by sequence specific hybridization and that is capable of extension of its length by the enzymatic incorporation of one or more additional nucleobase containing subunits. In some embodiments, a primer can be a nucleic acid (DNA or RNA). In some embodiments, a primer can be a nucleic acid analog (e.g. LNA or chimeric LNA molecule). In some embodiments, a primer can be a nucleic acid mimic so long as the polymerase enzyme can use said nucleic acid mimic as a substrate.

As used herein "probe" or "hybridization probe" refers to a polynucleobase strand that binds to a select target sequence by sequence specific hybridization. Non-limiting examples of polymers that can be used as probes include nucleic acid oligomers, (e.g. DNA, RNA, etc.) nucleic acid analog oligomers (e.g. locked nucleic acid (LNA)), nucleic acid mimic oligomers (e.g. peptide nucleic acid (PNA)) and chimeras). In some embodiments, a probe can be a nucleic acid (DNA or RNA). In some embodiments, a probe can be a nucleic acid analog (e.g. LNA or chimeric LNA molecule). In some embodiments, a probe can be a nucleic acid mimic.

To a large extent the terms "primer" and "probe" are functional definitions and are not exclusive. Thus, for example, a single oligonucleotide may be useful as either a probe or a primer depending on a particular use. To this end, the organization of Tables 2A and 2B is not limiting but merely reflects particular embodiments of the invention and also the uses of the particular oligonucleotides in the examples. The oligonucleotides identified as "primers" in Table 2A may be used as probes in appropriate contexts; similarly, the oligonucleotides identified as "probes" in Table 2B may be used as primers in appropriate contexts.

As used herein "sample" refers to any test sample of interest. For example, the sample can be sputum, mucus, bronchoalveolar lavage, pleural effusion, or cerebral spinal fluid. The sample may, for example, be a derivative of sputum, mucus, bronchoalveolar lavage, pleural effusion, or cerebral spinal fluid. The sample may, for example, be a biopsy, a smear or a colony from a culture or subculture. The sample can be from a human or a non-human animal. The sample can be an environmental sample, for example soil and water.

As used herein, "sequence specifically" refers to hybridization by base-pairing through hydrogen bonding. Non-limiting examples of standard base pairing include adenine base pairing with thymine or uracil and guanine base pairing with cytosine. Other non-limiting examples of base-pairing motifs include, but are not limited to: adenine base pairing with any of: 5-propynyl-uracil, 2-thio-5-propynyl-uracil, 2-thiouracil or 2-thiothymine; guanine base pairing with any of: 5-methylcytosine or pseudoisocytosine; cytosine base pairing with any of: hypoxanthine, N9-(7-deaza-guanine) or N9-(7-deaza-8-aza-guanine); thymine or uracil base pairing with any of: 2-aminopurine, N9-(2-amino-6-chloropurine) or N9-(2,6-diaminopurine); and N8-(7-deaza-8-aza-adenine), being a universal base, base-pairing with any other nucleobase, such as for example any of: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine) or N9-(7-deaza-8-aza-guanine) (See: Seela et al., *Nucl. Acids, Res.:* 28(17): 3224-3232 (2000)). It is to be understood however that a probe or primer can hybridize with sequence specificity even in the presence of one or more point mutations, insertions or deletions such that the remaining complementary nucleobases are able to base-pair.

As used herein "synthetic oligonucleotide" refers to any polynucleobase strand (e.g. a DNA oligonucleotide, RNA oligonucleotide, morpholino oligomer or PNA oligomer) that is synthetically assembled by human intervention. In some embodiments a synthetic oligonucleotide comprises at least one atom or moiety at a location at which it does not occur in naturally occurring nucleobases.

As used herein a "labeled" polynucleobase strand, such as a labeled synthetic oligonucleotide, refers to a polynucleobase strand that may be detected by at least one method in the context of other molecules and/or components present in an assay. In some embodiments the label emits a signal directly (e.g., P-32). The signal may be constitutive or may only be emitted when appropriate conditions are provided. In some embodiments the label is capable of specifically binding to a capture probe that facilitates detection of the presence of the label indirectly (e.g., and ELISA assay). One example of a label is a fluorescent moiety attached to a polynucleobase strand. Another example is a biotin molecule capable of specifically binding to streptavidin probe that facilitates detection of the presence of the label indirectly (e.g., and ELISA assay). In some embodiments the label comprises at least one moiety that is not present in a naturally occurring nucleobase.

As used herein "target" or "target sequence" refers to a nucleobase sequence (often a subsequence of the entire molecule) of a polynucleobase strand sought to be determined or to which a primer or probe is designed to hybridize with sequence specificity. The target sequence can be a subsequence of rRNA, rDNA, cDNA, genomic DNA and/or mRNA of an organism of interest (e.g. *Mycobacterium tuberculosis*). The target sequence can be a subsequence of a polynucleobase strand (including a polynucleobase strand of an amplicon) produced from a nucleic acid amplification reaction. Non-limiting examples of nucleic acid amplification reactions include: Polymerase Chain Reaction (PCR), Ligase Chain Reaction (LCR), Strand Displacement Amplification (SDA), Transcription-Mediated Amplification (TMA), Rolling Circle Amplification (RCA)), Cycling Probe Technology (CPT), Loop-Mediated Isothermal Amplification (LAMP), Linear Target Isothermal Multimerization and Amplification (LIMA), and Q-beta replicase amplification.

As used herein "template nucleic acid" refers to a polynucleobase strand that sets the nucleobase sequence of new strands formed by practice of an amplification reaction.

Other definitions are provided throughout the application.

General

It is to be understood that the discussion set forth below in this "General" section can pertain to some, or to all, of the various embodiments of the invention described herein.

Polynucleobase strands of various types and labeling configurations are commercially available from vendors. These include nucleic acid (both DNA and RNA), morpholino, locked nucleic acid (LNA) and peptide nucleic acid (PNA) probes and primers. Said oligomer probes and primers are available in unlabeled form, in single labeled form, in dual labeled form as well as in multi-label form. Labels on the dual and multi-labeled form can, in some embodiments, be the same label. Labels on the dual and multi-labeled form can, in some embodiments, be different labels. Probes and primers useful for embodiments of this invention can be custom ordered, prepared and then shipped worldwide by commercial vendors in a matter of days.

Nucleic acid hybridization is a fundamental process in molecular biology. Probe-based assays are useful in the detection, quantitation and/or analysis of nucleic acids. Primer-based assays are likewise useful in the detection, quantitation and/or analysis of nucleic acids. Nucleic acid probes have long been used to analyze samples for the presence of nucleic acid from bacteria, fungi, virus or other organisms and are also useful in examining genetically-based disease states or clinical conditions of interest.

Probes and primers are used under suitable hybridization conditions. The extent and stringency of hybridization is controlled by a number of factors well known to those of ordinary skill in the art. These factors include the concentration of chemical denaturants such as formamide, ionic strength, detergent concentration, pH, the presence or absence of chaotropic agents, temperature, the concentrations of the probe(s) and quencher(s) and the time duration of the hybridization reaction. Suitable hybridization conditions can be experimentally determined by examining the effect of each of these factors on the extent and stringency of the hybridization reaction until conditions providing the required extent and stringency are found. When properly applied, suitable hybridization conditions result in sequence specific hybridization.

Hybridization of probes and primers to their complementary sequences produce hybridization complexes (generally a duplex formed by the hybridization of the probe or primer to its target sequence). Said hybridization complexes can be detected by numerous methods available to and known by the ordinary practitioner. Said methods can be employed by routine experimentation. Some examples of such complex determinations are found in the Examples below.

In the context of some embodiments of the present invention, the determination of probe/target complexes formed by the hybridization of probes to amplicon products is representative of the presence and/or amount (if quantifying the assay) of target sequence available in the original sample. Similarly, the absence of a probe/target complex that can be formed from an amplification reaction (and thereby determined) is evidence of the lack of target in the sample to be tested. Thus, methods embodiments of the invention disclosed herein can be used to determine the presence absence or amount of target sequences in a sample of interest. Because of the nature of the unique probes and primers disclosed herein, said methods can generally be used to determine the presence, absence or amount of *Mycobacterium Tuberculosis* in a sample or samples of interest. In the examples below, the presence, absence or amount to probe/target complex that correlates with the presence, absence or amount of *Mycobacterium tuberculosis* can be determined using an Enzyme-linked immunosorbent assay (ELISA).

Specificity of Primer Sets and Capture Probes

In the examples shown below, the MTB ponA gene was selected as a target for the production of PCR primers and associated capture/binding probes. Gene ponA is involved in the synthesis of the unique bacterial wall of MTB and it is highly conserved (99.75%, DNA sequence analysis) within all members of the *Mycobacterium tuberculosis* complex. The closest related ponA is from the environmental *Mycobacterium Kansasii* with only 84% DNA sequence similarity (FIGS. 1A to 1E) and 85% amino acid identities. The about 15% difference in amino acid sequence between *M. tuberculosis* and *M. kansassii* represents a significant evolutionary difference; comparable to the evolutionary distance between *M. kansasii* and unrelated *Corynebacterium* species (Table 1). These observations suggest that within pathogenic MTB the ponA protein and its corresponding gene may have stopped evolving. Therefore, by targeting ponA, this invention provides for extreme specificity to detect only members of the *Mycobacterium* complex.

TABLE 1

MTB ponA has very low homology with other Mycobacteria and related bacteria.

| ponA Bacteria | Homology with MTB |
|---|---|
| *M. kansasii* | 85% |
| *M. marinum* "M" | 84% |
| *M. ulcerans* Agy99 | 84% |
| *M. avium* Para TB | 83% |
| *M. avium* 104 | 83% |
| *M. leprae* | 80% |
| M. sp JLS | 79% |
| M. sp KMS | 79% |
| M. sp JDM601 | 78% |
| *M. smegmatis* | 78% |
| *M. abscesus* | 76% |
| *Rodococcus* | 75% |
| *Nocardia* | 74% |
| *Gordonia* | 72% |
| *Corynebacterium* | 70% |

Because the ponA gene is so distinct and conserved, the inventors have determined and shown in the examples below that it is possible to design highly specific probes and primers that can be used to determine *Mycobacterium tuberculosis*. The inventors have likewise determined that it is possible to achieve suitable results even if the probes or primers are altered as compared with the exact sequences shown in Table 2. For example, probes that are slightly longer or shorter than those listed in Table 2 but that are based on sequence shown in FIGS. 1A to 1E can be used. Similarly, probes or primers that comprise one or two point mutations as compared with the probes or primers listed in Table 2 provide acceptable selectivity and specificity in certain embodiments.

Quantitative Capabilities

Quantitative asymmetric PCR is designed to provide "linear" amplification. To achieve this, asymmetric PCR uses an unequal (asymmetric) concentration of forward and reverse primers. In some embodiments of this invention, the molar ratio of a biotinylated first primer to a non-biotinylated second primer was 40:1 (see the Examples). Conventional PCR (symmetric) utilizes equal (1:1) molar ratio of forward and reverse primers, which produce double stranded amplicons and a very narrow range of quantification. Amplicons generated in one cycle serve as templates for subsequent cycles thereby generating an exponential amplification. A PCR with a single primer produces a perfectly linear production of product (for example 60 copies generated in 60 cycles from one target DNA copy). However, this process produces too few copies to be detected reliably in the majority of specimens where input templates are in low copy number. Asymmetric PCR (as used in some embodiments of this invention) utilizes an unequal (asymmetric) concentration of the two primers; the unlabeled primer in very low but sufficient concentration to reach detectable levels while maintaining linear amplification. The range of quantification, if any, of conventional PCR resides below 25 genome copies. The presence of additional copies renders the assay non-quantitative.

In some embodiments of this invention, asymmetric PCR can quantify organisms across 4-5 logs. In some embodiments, numbers of MTB were quantified accurately from 5,000 down to 0.01 genome equivalents in human specimens (FIG. 6).

Control Over the Range of Quantification

Figure 3:
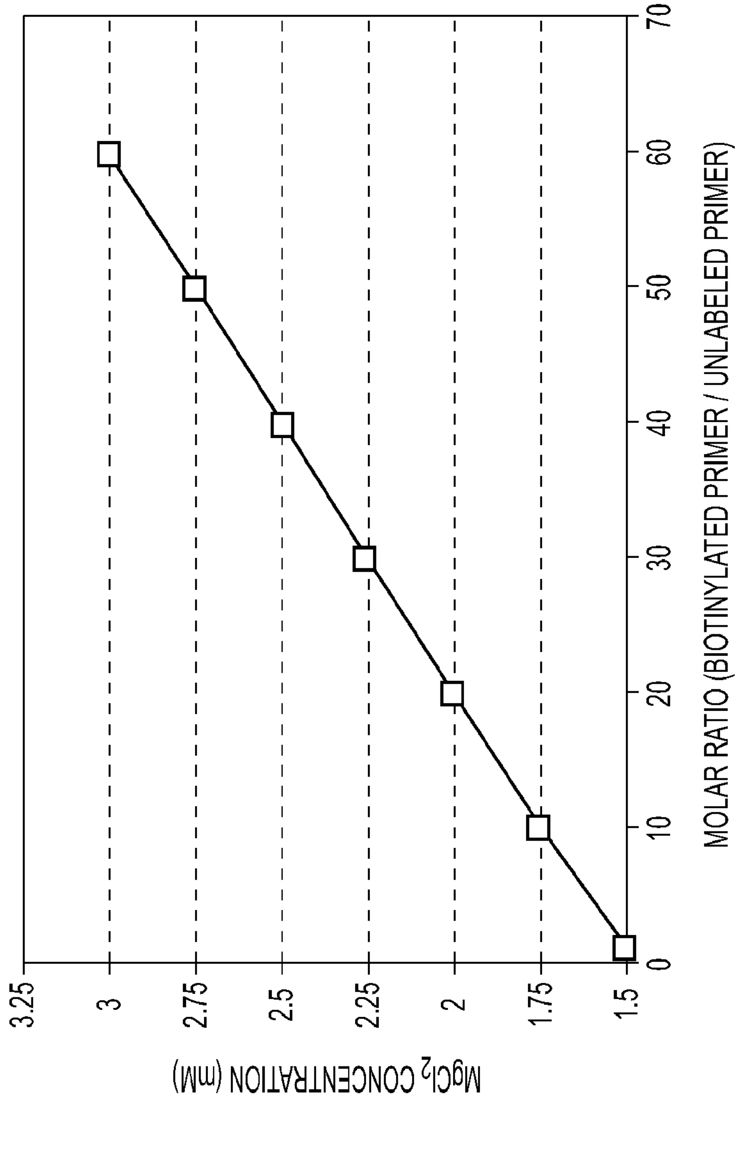
FIG. 3 shows a graphical illustration of the modulation of $MgCl_2$ concentration as a function of molar ratio of biotinylated primer to unlabeled primer. As shown in the figure, as the molar ratio of primers utilized increases, the required amount of $MgCl_2$ proportionally increases in the PCR reaction in order to maintain optimal asymmetric amplification.

In some embodiments, wider ranges of linear amplification can be obtained at increasingly higher molar ratios of biotinylated reverse primer to forward primer. In some embodiments these high primer ratios are possible with linearly higher $MgCl_2$ concentrations (FIG. 3). In some embodiments these high concentrations of $MgCl_2$ are beyond what it is required in a conventional PCR (1:1), and in certain cases will impede successful amplification. On the other hand, at conventional concentrations of $MgCl_2$, asymmetric PCR may, in certain circumstances fail when molar ratios of reverse primer to forward primer are greater than 10:1. For certain embodiments of this invention, $MgCl_2$ concentration can be optimized by using the information provided herein in combination with routine experimentation.

Figure 6:
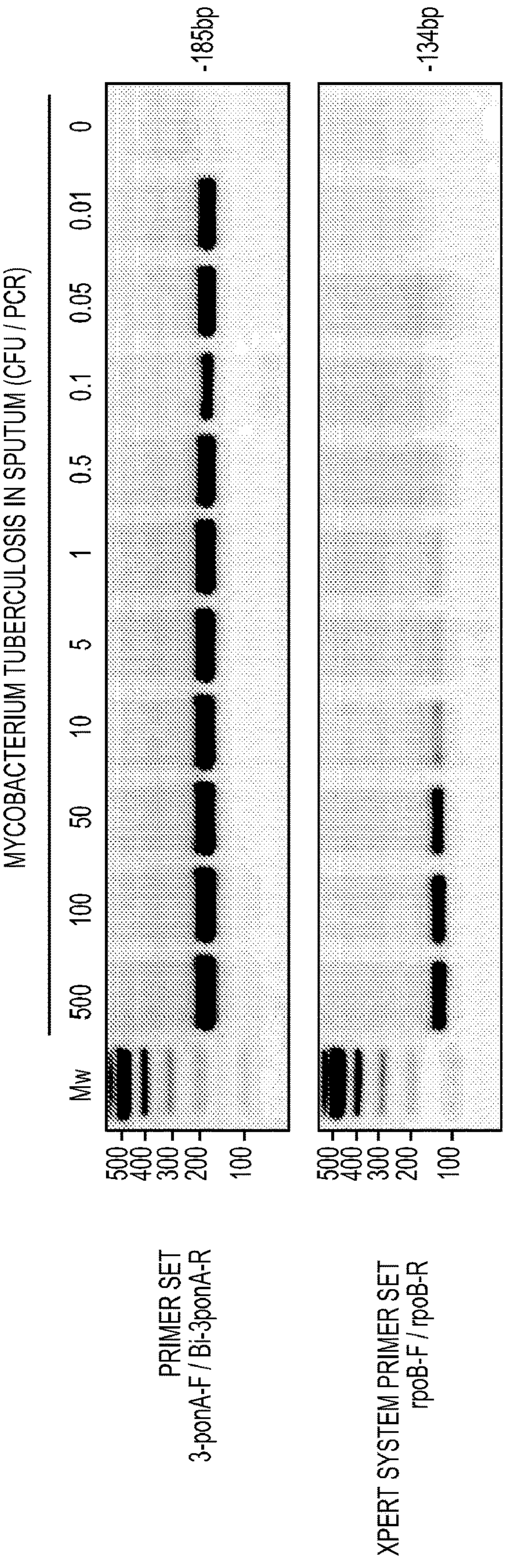
FIG. 6 shows gel images illustrating analytical sensitivity in sputum specimens from hospitalized subjects of primers 3-ponA-F (SEQ ID NO: 11) and Bi-3-ponA-R (SEQ ID NO: 14) compared side by side to the best primer set from current technology rpoB-F (SEQ ID NO: 45) and rpoB-R (SEQ ID NO: 46) included in the Xpert MTB/RIF system.
Figure 7:
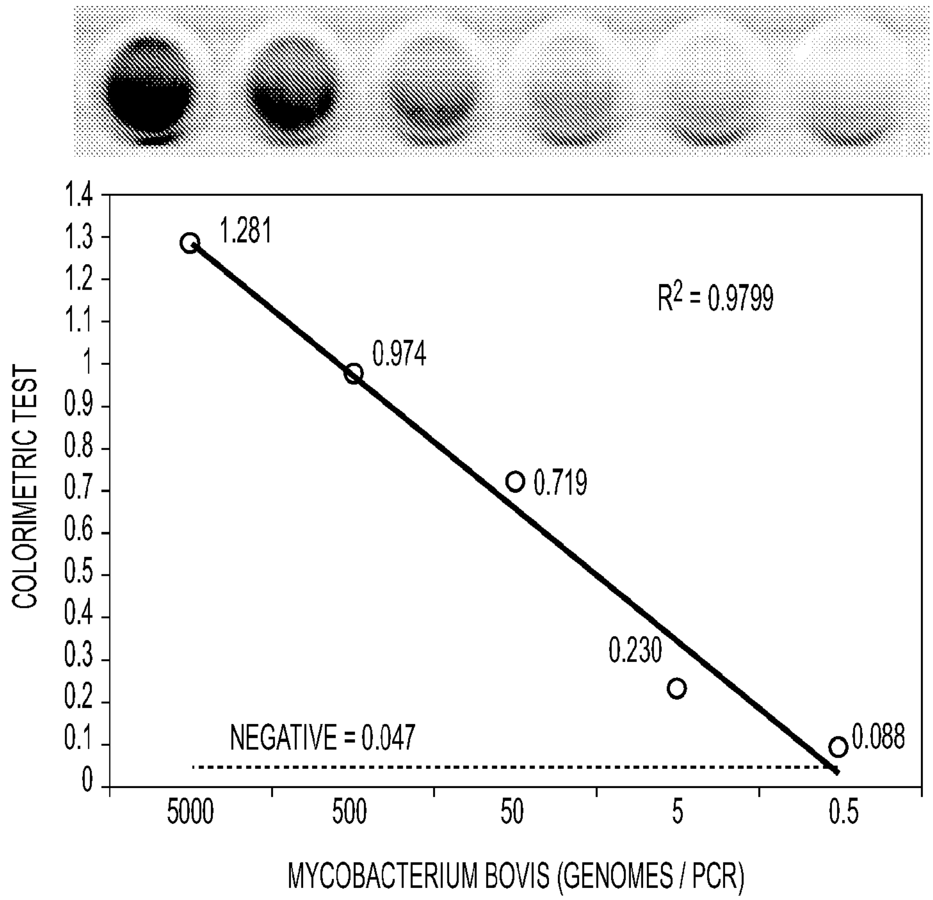
FIG. 7 shows capture probe ELISA images (upper panel) and a graphical illustration (lower panel) of quantitative asymmetric PCR results in ten-fold serial dilutions of *Mycobacterium bovis* (MTB complex) using a human specimen. Colorimetric detection and quantification by capture probe ELISA was performed with primer set 3-ponA-F (SEQ ID NO: 11) and Bi-3-ponA-R (SEQ ID NO: 14), and probe 3-ponA-probe (SEQ ID NO: 27) in sputum samples of hospitalized patients. Genomic DNA dilutions of *M. tuberculosis* vaccine strain BCG (5,000 to 0.5 genomes/PCR) contained equal amounts of human genomic DNA.

In some embodiments $MgCl_2$, concentrations for asymmetric PCR are chosen in accordance with the concentrations provided in FIG. 6. In other embodiments $MgCl_2$, concentrations for asymmetric PCR are not chosen in accordance with the concentrations provided in FIG. 6. It is well within the level of skill in the art to try several different parameters for PCR, including for asymmetric PCR, in order to identify conditions for use in a particular assay.

Quantifying Out of Range Specimens

In some embodiments, the quantification range expected for MTB quantitative PCR is 5,000 to 0.5 copies per PCR reaction. Without wishing to be bound by theory, it is anticipated that the number of organisms present in human specimens should be within this range. It is anticipated that the numbers of MTB should be low in smear-negative respiratory secretions and high in culture-positive secretions. In some embodiments, there may be extreme ranges of organism loads in a sample. To quantify extreme ranges of organism loads (out of range) MTB asymmetric PCR can be adjusted according to methods known in the art. For example, samples that show the highest counts can be re-tested after diluting the DNA (1/10 or 1/100), and the count obtained multiplied by the dilution factor when calculating MTB load. Likewise, samples showing the lowest number of organisms (or no organisms) can be retested by asymmetric PCR with the primers at a lower ratio of about, for example, 20:1 instead of 40:1. At about a 20:1 ratio of primers, the signal intensity will be higher and the detectable (linear) range of quantification will be 500 to 0.05 copies per reaction. If the sample remains out of range, it will be qualified as <0.05 genomes or colony forming units equivalents (CFUe) per reaction.

Flexibility of Design

Unlike conventional PCR that amplifies double stranded PCR products, MTB asymmetric PCR amplifies mostly single stranded PCR products. Detection of single stranded PCR amplicons can be easily accomplished using immobilized probe methodology. Substitution of the ELISA capture-probe detection system described in embodiments of this invention with any of the available technologies based on capture-probe detection known to one of skill in the art will be routine and may improve sensitivity and specificity. For example, a nanoparticle base detection system of single stranded labeled amplicons will greatly improve the signal to background ratio which can allow, in some embodiments: 1) the incorporation of additional primers and probes to detect simultaneously MTB drug resistance at the molecular level; 2) extension of the range of MTB quantification beyond 5 logs; and 3) reduction of the number of PCR cycles for faster turnaround time.

Probe & Primer Embodiments

In an aspect this disclosure provides synthetic oligonucleotides. The synthetic oligonucleotides may be used as probes and/or primers in nucleic acid amplification and/or detection methods, for example. In general the synthetic oligonucleotides of this disclosure may be used as a "probe" and/or as a "primer" depending on the context. While a particular synthetic oligonucleotide may be described in relation to a certain embodiment as a "probe" that designation is not intended to be limiting and the same synthetic oligonucleotide may be used. In some embodiments the synthetic oligonucleotide may alternatively be used as a "primer" in a different embodiment.

In some embodiments the synthetic oligonucleotide (i) comprises or consists of from 12 to 100, from 12 to 50, from 12 to 25, from 12 to 18, from 20 to 100, from 20 to 80, from 20 to 60, from 20 to 40, from 20 to 30, or from 23 to 27 nucleobase subunits; and (ii) possesses a nucleobase sequence that: 1) is identical in nucleobase sequence to a subsection of any one of SEQ ID NOS: 1-44; 2) is identical in nucleobase sequence to a subsection of any one of SEQ ID NOS: 1-44 except for the presence of one single point mutation as compared with the any one of SEQ ID NOS: 1-44; or 3) is identical in nucleobase sequence to a subsection of any one of SEQ ID NOS: 1-44 except for the presence of two point mutations as compared with the any one of SEQ ID NOS: 1-44.

In some embodiments the synthetic oligonucleotide has a calculated binding value in the range of 60 to 74 inclusive, wherein the nucleobase sequence of said synthetic oligonucleotide: (i) is selected to be from 23 to 27 nucleobase subunits in length; and (ii) possesses a nucleobase sequence that: 1) is identical in nucleobase sequence to a subsection of SEQ ID NO: 1; 2) is identical in nucleobase sequence to a subsection of SEQ ID NO: 1 except for the presence of one single point mutation as compared with SEQ ID NO: 1; 3) is identical in nucleobase sequence to a subsection of SEQ ID NO: 1 except for the presence of two point mutations as compared with SEQ ID NO: 1; or 4) is complementary to any one of 1) to 3). For example, the synthetic oligonucleotide may possess a nucleobase sequence that comprises or consists of SEQ ID NO: 11. Collectively, any synthetic oligonucleotide defined by this paragraph is referred to as Primer 1.

In some embodiments the synthetic oligonucleotide has a calculated binding value in the range of 52 to 66 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a subsection of SEQ ID NO: 4; 2) is identical in nucleobase sequence to a subsection of SEQ ID NO: 4 except for the presence of one single point mutation as compared with SEQ ID NO: 4; 3) is identical in nucleobase sequence to a subsection of SEQ ID NO: 4 except for the presence of two point mutations as compared with SEQ ID NO: 4; or 4) is complementary to any one of 1) to 3). For example, the synthetic oligonucleotide may possess a nucleobase sequence that comprises or consists of SEQ ID NO: 14. Collectively, any synthetic oligonucleotide defined by this paragraph is referred to as Primer 2.

In some embodiments the synthetic oligonucleotide has a calculated binding value in the range of 52 to 66 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a subsection of SEQ ID NO: 5; 2) is identical in nucleobase sequence to a subsection of SEQ ID NO: 5 except for the presence of one single point mutation as compared with SEQ ID NO: 5; 3) is identical in nucleobase sequence to a subsection of SEQ ID NO: 5 except for the presence of two point mutations as compared with SEQ ID NO: 5; or 4) is complementary to any one of 1) to 3). For example, the synthetic oligonucleotide may possess a nucleobase sequence that comprises or consists of SEQ ID NO: 15. Collectively, any synthetic oligonucleotide defined by this paragraph is referred to as Primer 3.

In some embodiments the synthetic oligonucleotide has a calculated binding value in the range of 51 to 65 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a subsection of SEQ ID NO: 8; 2) is identical in nucleobase sequence to a subsection of SEQ ID NO: 8 except for the presence of one single point mutation as compared with SEQ ID NO: 8; or 3) is identical in nucleobase sequence to a subsection of SEQ ID NO: 8 except for the presence of two point mutations as compared with SEQ ID NO: 8; or 4) is complementary to any one of 1) to 3). For example, the synthetic oligonucleotide may possess a nucleobase sequence that comprises or consists of SEQ ID NO: 18. Collectively, any synthetic oligonucleotide defined by this paragraph is referred to as Primer 4.

In some embodiments the synthetic oligonucleotide has a calculated binding value in the range of 51 to 65 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a subsection of SEQ ID NO: 7; 2) is identical in nucleobase sequence to a subsection of SEQ ID NO: 7 except for the presence of one single point mutation as compared with SEQ ID NO: 7; or 3) is identical in nucleobase sequence to a subsection of SEQ ID NO: 7 except for the presence of two point mutations as compared with SEQ ID NO: 7; or 4) is complementary to any one of 1) to 3). For example, the synthetic oligonucleotide may possess a nucleobase sequence that comprises or consists of SEQ ID NO: 17. Collectively, any synthetic oligonucleotide defined by this paragraph is referred to as Primer 5.

In some embodiments the synthetic oligonucleotide has a calculated binding value in the range of 48 to 62 inclusive, wherein the nucleobase sequence of said synthetic oligonucleotide: (i) is selected to be from 18 to 21 nucleobase subunits in length; and (ii) possess a nucleobase sequence that: 1) is identical in nucleobase sequence to a subsection of SEQ ID NO: 10; 2) is identical in nucleobase sequence to a subsection of SEQ ID NO: 10 except for the presence of one single point mutation as compared with SEQ ID NO: 10; 3) is identical in nucleobase sequence to a subsection of SEQ ID NO: 10 except for the presence of two point mutations as compared with SEQ ID NO: 10; or 4) is complementary to any one of 1) to 3). For example, the synthetic oligonucleotide may possess a nucleobase sequence that comprises or consists of SEQ ID NO: 20. Collectively, any synthetic oligonucleotide defined by this paragraph is referred to as Primer 6.

In some embodiments the synthetic oligonucleotide has a calculated binding value in the range of 48 to 62 inclusive, wherein the nucleobase sequence of said synthetic oligonucleotide: (i) is selected to be from 18 to 21 nucleobase subunits in length; and (ii) possesses a nucleobase sequence that: 1) is identical in nucleobase sequence to a subsection of SEQ ID NO: 34; 2) is identical in nucleobase sequence to a subsection of SEQ ID NO: 34 except for the presence of one single point mutation as compared with SEQ ID NO: 34; 3) is identical in nucleobase sequence to a subsection of SEQ ID NO: 34 except for the presence of two point mutations as compared with SEQ ID NO: 34; or 4) is complementary to any one of 1) to 3). For example, the synthetic oligonucleotide may possess a nucleobase sequence that comprises or consists of SEQ ID NO: 36. Collectively, any synthetic oligonucleotide defined by this paragraph is referred to as Primer 7.

In some embodiments the synthetic oligonucleotide has a calculated binding value in the range of 55 to 69 inclusive, wherein the nucleobase sequence of said synthetic oligonucleotide: (i) is selected to be from 23 to 26 nucleobase subunits in length; and (ii) possesses a nucleobase sequence that: 1) is identical in nucleobase sequence to a subsection of SEQ ID NO: 21; 2) is identical in nucleobase sequence to a subsection of SEQ ID NO: 21 except for the presence of one single point mutation as compared with SEQ ID NO: 21; 3) is identical in nucleobase sequence to a subsection of SEQ ID NO: 21 except for the presence of two point mutations as compared with SEQ ID NO: 21; or 4) is complementary to any one of 1) to 3). For example, the synthetic oligonucleotide may possess a nucleobase sequence that comprises or consists of SEQ ID NO: 27. Collectively, any synthetic oligonucleotide defined by this paragraph is referred to as Probe 1.

In some embodiments the synthetic oligonucleotide has a calculated binding value in the range of 48 to 62 inclusive, wherein the nucleobase sequence of said synthetic oligonucleotide: (i) is selected to be from 20 to 23 nucleobase subunits in length; and (ii) possesses a nucleobase sequence that: 1) is identical in nucleobase sequence to a subsection of SEQ ID NO: 24; 2) is identical in nucleobase sequence to a subsection of SEQ ID NO: 24 except for the presence of one single point mutation as compared with SEQ ID NO: 24; 3) is identical in nucleobase sequence to a subsection of SEQ ID NO: 24 except for the presence of two point mutations as compared with SEQ ID NO: 24; or 4) is complementary to any one of 1) to 3). For example, the synthetic oligonucleotide may possess a nucleobase sequence that comprises or consists of SEQ ID NO: 30. Collectively, any synthetic oligonucleotide defined by this paragraph is referred to as Probe 2.

In some embodiments the synthetic oligonucleotide has a calculated binding value in the range of 52 to 66 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a subsection of SEQ ID NO: 25; 2) is identical in nucleobase sequence to a subsection of SEQ ID NO: 25 except for the presence of one single point mutation as compared with SEQ ID NO: 25; 3) is identical in nucleobase sequence to a subsection of SEQ ID NO: 25 except for the presence of two point mutations as compared with SEQ ID NO: 25; or 4) is complementary to any one of 1) to 3). For example, the synthetic oligonucleotide may possess a nucleobase sequence that comprises or consists of SEQ ID NO: 31. Collectively, any synthetic oligonucleotide defined by this paragraph is referred to as Probe 3.

In some embodiments the synthetic oligonucleotide has a calculated binding value in the range of 52 to 66 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a subsection of SEQ ID NO: 38; 2) is identical in nucleobase sequence to a subsection of SEQ ID NO: 38 except for the presence of one single point mutation as compared with SEQ ID NO: 38; 3) is identical in nucleobase sequence to a subsection of SEQ ID NO: 38 except for the presence of two point mutations as compared with SEQ ID NO: 38; or 4) is complementary to any one of 1) to 3). For example, the synthetic oligonucleotide may possess a nucleobase sequence that comprises or consists of SEQ ID NO: 42. Collectively, any synthetic oligonucleotide defined by this paragraph is referred to as Probe 4.

In some embodiments the synthetic oligonucleotide has a calculated binding value in the range of 52 to 66 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a subsection of SEQ ID NO: 39; 2) is identical in nucleobase sequence to a subsection of SEQ ID NO: 39 except for the presence of one single point mutation as compared with SEQ ID NO: 39; 3) is identical in nucleobase sequence to a subsection of SEQ ID NO: 39 except for the presence of two point mutations as compared with SEQ ID NO: 39; or 4) is complementary to any one of 1) to 3). For example, the synthetic oligonucleotide may possess a nucleobase sequence that comprises or consists of SEQ ID NO: 43. Collectively, any synthetic oligonucleotide defined by this paragraph is referred to as Probe 5.

In some embodiments the synthetic oligonucleotide is labeled. In some embodiments the label is a biotin moiety. In some embodiments the biotin moiety is attached to the 5' end of the synthetic oligonucleotide.

Method Embodiments

In another aspect this disclosure provides methods that utilize at least one synthetic oligonucleotide of the invention to determine the presence, absence and/or amount of *mycobacterium tuberculosis* in a sample.

In some embodiments the methods comprise contacting a sample obtained from a subject with at least one synthetic oligonucleotide selected from SEQ ID NOS: 1-44 and detecting hybridization of the synthetic oligonucleotide with a homologous sequence present in the sample.

In some embodiments the methods comprise contacting a sample obtained from a subject with at least one synthetic oligonucleotide selected from SEQ ID NOS: 1-44 and amplifying at least a portion of a template nucleic acid to thereby produce an amplicon product. In some embodiments the amplicon product is contacted with at least one second synthetic oligonucleotide selected from SEQ ID NOS: 1-44 and determining whether or not said at least one second synthetic oligonucleotide hybridizes to said amplicon product.

In some embodiments the methods comprise: i) contacting a template nucleic acid obtained from a subject sample, under nucleic acid amplification conditions, with: 1) a first primer that is a synthetic oligonucleotide according to any embodiment of Primer 1; and 2) a second primer that is a synthetic oligonucleotide according to any embodiment of Primer 2; ii) amplifying at least a portion of said template to thereby produce an amplicon product; iii) contacting said amplicon product with a probe that is a synthetic oligonucleotide according to any embodiment of Probe 1; and iv) determining whether or not said probe hybridizes to said amplicon product to thereby determine the presence, absence and/or amount of *mycobacterium tuberculosis* in said sample.

In some embodiments the methods comprise: i) contacting a template nucleic acid obtained from a subject sample, under nucleic acid amplification conditions, with: 1) a first primer that is a synthetic oligonucleotide according to any embodiment of Primer 3; and 2) a second primer that is a synthetic oligonucleotide according to any embodiment of Primer 4; ii) amplifying at least a portion of said template to thereby produce an amplicon product; iii) contacting said amplicon product with a probe that is a synthetic oligonucleotide according to any embodiment of Probe 2; and iv) determining whether or not said probe hybridizes to said amplicon product to thereby determine the presence, absence and/or amount of *mycobacterium tuberculosis* in said sample.

In some embodiments the methods comprise: i) contacting a template nucleic acid obtained from a subject sample, under nucleic acid amplification conditions, with: 1) a first primer that is a synthetic oligonucleotide according to any embodiment of Primer 5; and 2) a second primer that is a synthetic oligonucleotide according to any embodiment of Primer 6; ii) amplifying at least a portion of said template to thereby produce an amplicon product; iii) contacting said amplicon product with a probe that is a synthetic oligonucleotide according to any embodiment of Probe 3; and iv) determining whether or not said probe hybridizes to said amplicon product to thereby determine the presence, absence and/or amount of *mycobacterium tuberculosis* in said sample.

In some embodiments the methods comprise: i) contacting a template nucleic acid obtained from a subject sample, under nucleic acid amplification conditions, with: 1) a first primer that is a synthetic oligonucleotide according to any embodiment of Primer 3; and 2) a second primer that is a synthetic oligonucleotide according to any embodiment of Primer 4; ii) amplifying at least a portion of said template to thereby produce an amplicon product; iii) contacting said amplicon product with a probe that is a synthetic oligonucleotide according to any embodiment of Probe 4; and iv) determining whether or not said probe hybridizes to said amplicon product to thereby determine the presence, absence and/or amount of *mycobacterium tuberculosis* in said sample.

In some embodiments the methods comprise: i) contacting a template nucleic acid obtained from a subject sample, under nucleic acid amplification conditions, with: 1) a first primer that is a synthetic oligonucleotide according to any embodiment of Primer 5; and 2) a second primer that is a synthetic oligonucleotide according to any embodiment of Primer 7; ii) amplifying at least a portion of said template to thereby produce an amplicon product; iii) contacting said amplicon product with a probe that is a synthetic oligonucleotide according to any embodiment of Probe 5; and iv) determining whether or not said probe hybridizes to said amplicon product to thereby determine the presence, absence and/or amount of *mycobacterium tuberculosis* in said sample.

In some embodiments of the methods, said nucleic acid amplification conditions are asymmetric PCR amplification conditions.

In some embodiments of the methods, said determination of whether or not said probe hybridizes to said amplicon product is made by end-point analysis.

In some embodiments of the methods, said determination of whether or not said probe hybridizes to said amplicon product is made by real-time analysis.

In some embodiments the ratio of the concentration of the first primer to the second primer is at least 10:1, at least 15:1, at least 20:1, at least 25:1, at least 30:1, at least 35:1, at least 40:1, at least 45:1, or at least 50:1. In some embodiments the ratio of the concentration of the first primer to the second primer is from 1:10 to 1:20, from 1:10 to 1:30, from 1:10 to 1:40, from 1:10 to 1:50, or from 1:25 to 1:50.

In some embodiments the ratio of the concentration of the first primer to the second primer is from 1:1 to 1:2, from 1:1 to 1:5, or from 1: to 1:10.

In some embodiments of the methods, said nucleic acid amplification is quantitative. In some embodiments of the methods, said nucleic acid amplification is not quantitative.

In some embodiments of the methods, the sensitivity of the method is at least 50 *M. tuberculosis* genome equivalents, at least 10 *M. tuberculosis* genome equivalents, at least 5 *M. tuberculosis* genome equivalents, at least 1 *M. tuberculosis* genome equivalent, at least 0.5 *M. tuberculosis* genome equivalents, at least 0.1 *M. tuberculosis* genome equivalents, at least 0.05 *M. tuberculosis* genome equivalents, or at least 0.01 *M. tuberculosis* genome equivalents. In this context "at least X *M. tuberculosis* genome equivalents" means that the method is capable of detecting the presence of X or fewer genome equivalents in a control sample spiked with *M. tuberculosis* genomic DNA. In some embodiments one genomic equivalent of *M. tuberculosis* genomic DNA is 25 femtograms of isolated *M. tuberculosis* genomic DNA.

In some embodiments of the methods, said subject sample is obtained from a subject exhibiting at least one clinical symptom of *M. tuberculosis* infection.

In some embodiments of the methods, said subject sample is obtained from a subject who has not been diagnosed with *M. tuberculosis* infection.

In some embodiments of the methods, *mycobacterium tuberculosis* is detected in said sample, indicating that said subject is infected with *mycobacterium tuberculosis.*

In some embodiments of the methods, *mycobacterium tuberculosis* is not detected in said sample, indicating that said subject is not infected with *mycobacterium tuberculosis.*

In some embodiments of the methods, said subject sample is a sputum sample.

Screening Methods

Also provided are methods of screening subjects. The methods utilize at least one synthetic oligonucleotide of the invention to determine the presence, absence and/or amount of *mycobacterium tuberculosis* in a sample from a subject to be screened.

In some embodiments the methods comprise contacting a sample obtained from a subject to be screened with at least one synthetic oligonucleotide selected from SEQ ID NOS: 1-44 and detecting hybridization of the synthetic oligonucleotide with a homologous sequence present in the sample.

In some embodiments the methods comprise contacting a sample obtained from a subject subject to be screened with at least one synthetic oligonucleotide selected from SEQ ID NOS: 1-44 and amplifying at least a portion of a template nucleic acid to thereby produce an amplicon product. In some embodiments the amplicon product is contacted with at least one second synthetic oligonucleotide selected from SEQ ID NOS: 1-44 and determining whether or not said at least one second synthetic oligonucleotide hybridizes to said amplicon product.

In some embodiments the methods comprise: i) contacting a template nucleic acid obtained from a subject to be screened sample, under nucleic acid amplification conditions, with: 1) a first primer that is a synthetic oligonucleotide according to any embodiment of Primer 1; and 2) a second primer that is a synthetic oligonucleotide according to any embodiment of Primer 2; ii) amplifying at least a portion of said template to thereby produce an amplicon product; iii) contacting said amplicon product with a probe that is a synthetic oligonucleotide according to any embodiment of Probe 1; and iv) determining whether or not said probe hybridizes to said amplicon product to thereby determine the presence, absence and/or amount of *mycobacterium tuberculosis* in said sample.

In some embodiments the methods comprise: i) contacting a template nucleic acid obtained from a subject to be screened sample, under nucleic acid amplification conditions, with: 1) a first primer that is a synthetic oligonucleotide according to any embodiment of Primer 3; and 2) a second primer that is a synthetic oligonucleotide according to any embodiment of Primer 4; ii) amplifying at least a portion of said template to thereby produce an amplicon product; iii) contacting said amplicon product with a probe that is a synthetic oligonucleotide according to any embodiment of Probe 2; and iv) determining whether or not said probe hybridizes to said amplicon product to thereby determine the presence, absence and/or amount of *mycobacterium tuberculosis* in said sample.

In some embodiments the methods comprise: i) contacting a template nucleic acid obtained from a subject to be screened, under nucleic acid amplification conditions, with: 1) a first primer that is a synthetic oligonucleotide according to any embodiment of Primer 5; and 2) a second primer that is a synthetic oligonucleotide according to any embodiment of Primer 6; ii) amplifying at least a portion of said template to thereby produce an amplicon product; iii) contacting said amplicon product with a probe that is a synthetic oligonucleotide according to any embodiment of Probe 3; and iv) determining whether or not said probe hybridizes to said amplicon product to thereby determine the presence, absence and/or amount of *mycobacterium tuberculosis* in said sample.

In some embodiments the methods comprise: i) contacting a template nucleic acid obtained from a subject to be screened, under nucleic acid amplification conditions, with: 1) a first primer that is a synthetic oligonucleotide according to any embodiment of Primer 3; and 2) a second primer that is a synthetic oligonucleotide according to any embodiment of Primer 4; ii) amplifying at least a portion of said template to thereby produce an amplicon product; iii) contacting said amplicon product with a probe that is a synthetic oligonucleotide according to any embodiment of Probe 4; and iv) determining whether or not said probe hybridizes to said amplicon product to thereby determine the presence, absence and/or amount of *mycobacterium tuberculosis* in said sample.

In some embodiments the methods comprise: i) contacting a template nucleic acid obtained from a subject to be screened, under nucleic acid amplification conditions, with: 1) a first primer that is a synthetic oligonucleotide according to any embodiment of Primer 5; and 2) a second primer that is a synthetic oligonucleotide according to any embodiment of Primer 7; ii) amplifying at least a portion of said template to thereby produce an amplicon product; iii) contacting said amplicon product with a probe that is a synthetic oligonucleotide according to any embodiment of Probe 5; and iv) determining whether or not said probe hybridizes to said amplicon product to thereby determine the presence, absence and/or amount of *mycobacterium tuberculosis* in said sample.

In some embodiments of the methods, said nucleic acid amplification conditions are asymmetric PCR amplification conditions.

In some embodiments of the methods, said determination of whether or not said probe hybridizes to said amplicon product is made by end-point analysis.

In some embodiments of the methods, said determination of whether or not said probe hybridizes to said amplicon product is made by real-time analysis.

In some embodiments the ratio of the concentration of the first primer to the second primer is at least 10:1, at least 15:1, at least 20:1, at least 25:1, at least 30:1, at least 35:1, at least 40:1, at least 45:1, or at least 50:1. In some embodiments the ratio of the concentration of the first primer to the second primer is from 1:10 to 1:20, from 1:10 to 1:30, from 1:10 to 1:40, from 1:10 to 1:50, or from 1:25 to 1:50.

In some embodiments the ratio of the concentration of the first primer to the second primer is from 1:1 to 1:2, from 1:1 to 1:5, or from 1: to 1:10.

In some embodiments of the methods, said nucleic acid amplification is quantitative. In some embodiments of the methods, said nucleic acid amplification is not quantitative.

In some embodiments of the methods, the sensitivity of the method is at least 50 *M. tuberculosis* genome equivalents, at least 10 *M. tuberculosis* genome equivalents, at least 5 *M. tuberculosis* genome equivalents, at least 1 *M. tuberculosis* genome equivalent, at least 0.5 *M. tuberculosis* genome equivalents, at least 0.1 *M. tuberculosis* genome equivalents, at least 0.05 *M. tuberculosis* genome equivalents, or at least 0.01 *M. tuberculosis* genome equivalents. In this context "at least X *M. tuberculosis* genome equivalents" means that the method is capable of detecting the presence of X or fewer genome equivalents in a control sample spiked with *M. tuberculosis* genomic DNA. In some embodiments one genomic equivalent of *M. tuberculosis* genomic DNA is 25 femtograms of isolated *M. tuberculosis* genomic DNA.

In some embodiments of the methods, said subject sample is obtained from a subject exhibiting at least one clinical symptom of *M. tuberculosis* infection.

In some embodiments of the methods, said subject sample is obtained from a subject who has not been diagnosed with *M. tuberculosis* infection.

In some embodiments of the methods, *mycobacterium tuberculosis* is detected in said sample, indicating that said subject is infected with *mycobacterium tuberculosis.*

In some embodiments of the methods, *mycobacterium tuberculosis* is not detected in said sample, indicating that said subject is not infected with *mycobacterium tuberculosis.*

In some embodiments of the methods, said subject sample is a sputum sample.

Methods of Treatment

Methods of treating an *M. tuberculosis* infection are also provided. Generally the methods comprise identifying a subject comprising *M. tuberculosis* infection using a method (for example a screening method) of this disclosure (such as a method described above in this Methods section of the application) and administering an anti-*M. tuberculosis* agent to the subject to thereby treat the infection in the subject.

Anti-*M. tuberculosis* agents include, for example, isoniazid, rifampin, rifapentine, ethambutol, and pyrazinamide. In some embodiments the anti-*M. tuberculosis* agent is any chemical entity that is inhibits the growth of *M. tuberculosis* in an in vitro assay or an in vivo animal model.

Compositions

In another aspect this disclosure provides compositions. Generally the compositions comprise at least one synthetic oligonucleotide selected from SEQ ID NOS: 1-44. In some embodiments the compositions comprise at least two, at least three, at least four, at least five, at least six, at least seven, at least eight, at least nine, at least ten, or more synthetic oligonucleotides selected from SEQ ID NOS: 1-44. In some embodiments the compositions further comprise a template nucleic acid. In some embodiments the template nucleic acid is obtained from a subject.

In some embodiments the composition comprises a first primer that is a synthetic oligonucleotide according to any embodiment of Primer 1; and a second primer that is a synthetic oligonucleotide according to any embodiment of Primer 2. In some embodiments the composition further comprises a probe that is a synthetic oligonucleotide according to any embodiment of Probe 1. In some embodiments the composition further comprises a template nucleic acid.

In some embodiments the composition comprises a first primer that is a synthetic oligonucleotide according to any embodiment of Primer 3; and a second primer that is a synthetic oligonucleotide according to any embodiment of Primer 4. In some embodiments the composition further comprises a probe that is a synthetic oligonucleotide according to any embodiment of Probe 2. In some embodiments the composition further comprises a template nucleic acid.

In some embodiments the composition a first primer that is a synthetic oligonucleotide according to any embodiment of Primer 5; and a second primer that is a synthetic oligonucleotide according to any embodiment of Primer 6. In some embodiments the composition further comprises a probe that is a synthetic oligonucleotide according to Probe 3. In some embodiments the composition further comprises a template nucleic acid.

In some embodiments the composition comprises a first primer that is a synthetic oligonucleotide according to any embodiment of Primer 3; and a second primer that is a synthetic oligonucleotide according to any embodiment of Primer 4. In some embodiments the composition further comprises a probe that is a synthetic oligonucleotide according to Probe 4. In some embodiments the composition further comprises a template nucleic acid.

In some embodiments the composition comprises a first primer that is a synthetic oligonucleotide according to any embodiment of Primer 5; and a second primer that is a synthetic oligonucleotide according to any embodiment of Primer 7. In some embodiments the composition further comprises a probe that is a synthetic oligonucleotide according to any embodiment of Probe 5. In some embodiments the composition further comprises a template nucleic acid.

Kits and Systems

This disclosure also provides kits and systems that comprise at least one synthetic oligonucleotide of this disclosure. Generally the kits and systems comprise at least one synthetic oligonucleotide selected from SEQ ID NOS: 1-44. In some embodiments the kits and systems comprise at least two, at least three, at least four, at least five, at least six, at least seven, at least eight, at least nine, at least ten, or more synthetic oligonucleotides selected from SEQ ID NOS: 1-44. In some embodiments the kits and systems further comprise a template nucleic acid. In some embodiments the template nucleic acid is a positive control nucleic acid comprising a nucleic acid comprising SEQ ID NO: 47 or an amplifiable fragment thereof. In some embodiments the template nucleic acid is provided as a patient sample comprising a template nucleic acid.

In some embodiments the kit or system comprises a first primer that is a synthetic oligonucleotide according to any embodiment of Primer 1; and a second primer that is a synthetic oligonucleotide according to any embodiment of Primer 2. In some embodiments the kit or system further comprises a probe that is a synthetic oligonucleotide according to any embodiment of Probe 1. In some embodiments the kit or system further comprises a template nucleic acid. In some embodiments the template nucleic acid is a positive control nucleic acid comprising a nucleic acid comprising SEQ ID NO: 47 or an amplifiable fragment thereof. In some embodiments the template nucleic acid is provided as a patient sample comprising a template nucleic acid.

In some embodiments the kit or system comprises a first primer that is a synthetic oligonucleotide according to any embodiment of Primer 3; and a second primer that is a synthetic oligonucleotide according to any embodiment of Primer 4. In some embodiments the kit or system further comprises a probe that is a synthetic oligonucleotide according to any embodiment of Probe 2. In some embodiments the kit or system further comprises a template nucleic acid. In some embodiments the template nucleic acid is a positive control nucleic acid comprising a nucleic acid comprising SEQ ID NO: 47 or an amplifiable fragment thereof. In some embodiments the template nucleic acid is provided as a patient sample comprising a template nucleic acid.

In some embodiments the kit or system a first primer that is a synthetic oligonucleotide according to any embodiment of Primer 5; and a second primer that is a synthetic oligonucleotide according to any embodiment of Primer 6. In some embodiments the kit or system further comprises a probe that is a synthetic oligonucleotide according to Probe 3. In some embodiments the kit or system further comprises a template nucleic acid. In some embodiments the template nucleic acid is a positive control nucleic acid comprising a nucleic acid comprising SEQ ID NO: 47 or an amplifiable fragment thereof. In some embodiments the template nucleic acid is provided as a patient sample comprising a template nucleic acid.

In some embodiments the kit or system comprises a first primer that is a synthetic oligonucleotide according to any embodiment of Primer 3; and a second primer that is a synthetic oligonucleotide according to any embodiment of Primer 4. In some embodiments the kit or system further comprises a probe that is a synthetic oligonucleotide according to Probe 4. In some embodiments the kit or system further comprises a template nucleic acid. In some embodiments the template nucleic acid is a positive control nucleic acid comprising a nucleic acid comprising SEQ ID NO: 47 or an amplifiable fragment thereof. In some embodiments the template nucleic acid is provided as a patient sample comprising a template nucleic acid.

In some embodiments the kit or system comprises a first primer that is a synthetic oligonucleotide according to any embodiment of Primer 5; and a second primer that is a synthetic oligonucleotide according to any embodiment of Primer 7. In some embodiments the kit or system further comprises a probe that is a synthetic oligonucleotide according to any embodiment of Probe 5. In some embodiments the kit or system further comprises a template nucleic acid. In some embodiments the template nucleic acid is a positive control nucleic acid comprising a nucleic acid comprising SEQ ID NO: 47 or an amplifiable fragment thereof. In some embodiments the template nucleic acid is provided as a patient sample comprising a template nucleic acid.

In some embodiments the kit or system comprises a container such as a reaction vessel or packaging comprising the at least one synthetic oligonucleotide.

In some embodiments the kit is provided in a package.

Features of Certain Embodiments

Certain embodiments of this invention exhibit advantages for detection and quantification of *Mycobacterium tuberculosis* in clinical samples specimens. In some embodiments of the synthetic oligonucleotides, methods, compositions, kits, and/or systems of this disclosure at least one of the following advantages in optionally present:

- Accurate quantification of MTB loads in clinical samples in the range of 5,000 to 0.05 copies can be obtained.
- Detection of less than one genome of MTB in a human sample can be obtained.
- Optional use of higher concentrations of $MgCl_2$ in the PCR reaction facilitates a high forward to reverse primer ratio. This observation has led to a broadening of the clinically relevant range of amplification/quantification.
- A capability for an overall sensitivity>95% with a single sputum sample while maintaining a specificity>97% is obtainable. This translates into a sensitivity in smear-negative/culture positive TB patients of >93% (which compares well with the 72.5% sensitivity of the Xpert® MTB/RIF system in these type of patients). Moreover, the quantitative capabilities of the method may prove to be an added advantage for clinicians. Both the PCR and capture-probe detection phases have independent and complimentary quantitative capabilities that facilitate accurate estimates of bacterial load. This feature can be used to inform clinical treatment (i.e. patients with increased bacterial load require longer treatment) and help monitor response to anti-tuberculosis treatment.

Same-day diagnosis is achieved, minimizing patient losses and increasing the TB detection rate. The PCR amplification can be performed in 3-4 hours and the end-point detection can be performed in 1 hour or less if the ELISA capture-probe detection system is substituted with state of the art assay like nanoparticle detection of hybridized amplicons.

No requirement for excessive laboratory expertise. Such methods may be implemented in both high tech laboratory and low tech laboratory environments because they do not require UV light sources, lasers or fluorescent or radioactive labels.

In some embodiments of this invention, additional primers and probes could be easily incorporated to detect MTB genes that confer drug resistance (i.e. rifampicin, fluoroquinolones).

The assay could be easily applied to veterinary uses to detect Mycobacteria tuberculosis that, for example, infect bovine or other livestock.

EXAMPLES

Aspects of the present teachings can be further understood in light of the following examples, which should not be construed as limiting the scope of the present teachings in any way.

Synthetic oligonucleotides of this disclosure are provided in Tables 2A-2B. Comparative oligonucleotides are provided in Table 2C.

TABLE 2A

Primers

| SEQ ID NO | Primer Name | Sequence (5' to 3') | Length | CBV |
|---|---|---|---|---|
| 1 | Primer 1 genus - sense strand | TGACCGTTGCCGAAGGGGCGTTGTTGGC | 28 | 74 |
| 2 | Primer 1 genus - antisense strand | GCCAACAACGCCCCTTCGGCAACGGTCA | 28 | 74 |
| 3 | Primer 2 genus - sense strand | TTTCCCGAGACAGTGCCGCCCGATC | 25 | 66 |
| 4 | Primer 2 genus - antisense strand | GATCGGGCGGCACTGTCTCGGGAAA | 25 | 66 |
| 5 | Primer 3 genus - sense strand | CACAACCTAGCGGGTGGGCGGGATT | 25 | 66 |
| 6 | Primer 3 genus - antisense strand | AATCCCGCCCACCCGCTAGGTTGTG | 25 | 66 |
| 7 | Primer 4 genus - sense strand | AGACTTTCCCCAAACCGACCGAGGT | 25 | 64 |
| 8 | Primer 4 genus - antisense strand | ACCTCGGTCGGTTTGGGGAAAGTCT | 25 | 64 |
| 9 | Primer 5 genus - sense strand | GCGACTCCCACGCCGCCGCCGT | 22 | 62 |
| 10 | Primer 5 genus - antisense strand | ACGGCGGCGGCGTGGGAGTCGC | 22 | 62 |
| 11 | Primer 1 species - sense strand [3-ponA-F] | GACCGTTACCGAAGGGGCGTTGTTGG | 26 | 69 |
| 12 | Primer 1 species - antisense strand | CCAACAACGCCCCTTCGGTAACGGTC | 26 | 69 |
| 13 | Primer 2 species - sense strand | TTCCCGAGACAGTGCCGCCCGAT | 23 | 61 |
| 14 | Primer 2 species - antisense strand [Bi-3-ponA-R] | ATCGGGCGGCACTGTCTCGGGAA | 23 | 61 |
| 15 | Primer 3 species - sense strand [Bi-1-ponA-F] | ACAACATAGCGGGTGGGCGGGAT | 23 | 61 |
| 16 | Primer 3 species - antisense strand | ATCCCGCCCACCCGCTATGTTGT | 23 | 61 |

TABLE 2A-continued

| Primers | | | | |
|---|---|---|---|---|
| SEQ ID NO | Primer Name | Sequence (5' to 3') | Length | CBV |
| 17 | Primer 4 species - sense strand [2-ponA-F] | GACTTTCCCCAAACCGACCGAGG | 23 | 60 |
| 18 | Primer 4 species - antisense strand [1-ponA-R] | CCTCGGTCGGTTTGGGGAAAGTC | 23 | 60 |
| 19 | Primer 5 species - sense strand | CGACTCCCACGCCGCCGCCG | 20 | 57 |
| 20 | Primer 5 species - antisense strand [Bi-2-ponA-R] | CGGCGGCGGCGTGGGAGTCG | 20 | 57 |
| 33 | Primer 6 genus - sense strand | GTCCCCCGACCACCATTACCCTGG | 24 | 64 |
| 34 | Primer 6 genus - antisense strand | CCAGGGTAATGGTGGTCGGGGGAC | 24 | 64 |
| 35 | Primer 6 species - sense strand | TCCCCCGACCACCATTACCCTG | 22 | 58 |
| 36 | Primer 6 species - antisense strand [Bi-2-ponA-R-a] | CAGGGTAATGGTGGTCGGGGGA | 22 | 58 |

TABLE 2B

| Probes | | | | |
|---|---|---|---|---|
| SEQ ID NO | Probe Name | Sequence (5' to 3') | Length | CBV |
| 21 | Probe 1 genus - sense strand | AAACCAAGGCTCTCTCGCCGAATGACC | 27 | 69 |
| 22 | Probe 1 genus - antisense strand | GGTCATTCGGCGAGAGAGCCTTGGTTT | 27 | 69 |
| 23 | Probe 2 genus - sense strand | GTTGTCTACGGCTGTGTGGGTGGG | 24 | 63 |
| 24 | Probe 2 genus - antisense strand | CCCACCCACACAGCCGTAGACAAC | 24 | 63 |
| 25 | Probe 3 genus - sense strand | GGTCCCCCGACCACCATTACCCTGG | 25 | 67 |
| 26 | Probe 3 genus - antisense strand | CCAGGGTAATGGTGGTCGGGGGACC | 25 | 67 |
| 27 | Probe 1 species - sense strand [3-ponA-probe] | AACCAAGGCTCTCTCACCGAATGAC | 25 | 64 |
| 28 | Probe 1 species - antisense strand | GTCATTCGGTGAGAGAGCCTTGGTT | 25 | 64 |
| 29 | Probe 2 species - sense strand | TTGTCTACGGCTGTGTGGGTGG | 22 | 57 |
| 30 | Probe 2 species - antisense strand [1-ponA-probe] | CCACCCACACAGCCGTAGACAA | 22 | 57 |
| 31 | Probe 3 species - sense strand [2-ponA-probe] | GTCCCCCGACCACCATTACCCTG | 23 | 61 |

TABLE 2B-continued

| Probes | | | | |
|---|---|---|---|---|
| SEQ ID NO | Probe Name | Sequence (5' to 3') | Length | CBV |
| 32 | Probe 3 species - antisense strand | CAGGGTAATGGTGGTCGGGGGAC | 23 | 61 |
| 37 | Probe 4 genus - sense strand | CCGTCGTTGTCTACGGCTGTGTGGG | 25 | 66 |
| 38 | Probe 4 genus - antisense strand | CCCACACAGCCGTAGACAACGACGG | 25 | 66 |
| 39 | Probe 5 genus - sense strand | AGGTCGGTGGTTATGCCGGTGTGCCG | 26 | 69 |
| 40 | Probe 5 genus - antisense strand | CGGCACACCGGCATAACCACCGACCT | 26 | 69 |
| 41 | Probe 4 species - sense strand | CGTCGTTGTCTACGGCTGTGTGG | 23 | 60 |
| 42 | Probe 4 species - antisense strand [1-ponA-probe-a] | CCACACAGCCGTAGACAACGACG | 23 | 60 |
| 43 | Probe 5 species - sense strand [2-ponA-probe-a] | GGTCGGTGGTTATGCGGGTGTGCC | 24 | 64 |
| 44 | Probe 5 species - antisense strand | GGCACACCCGCATAACCACCGACC | 24 | 64 |

TABLE 2C

| Xpert ® MTB/RIF | | | | |
|---|---|---|---|---|
| SEQ ID NO | Name | Sequence (5' to 3') | Length | CBV |
| 45 | rpoB-F | GGCCGGTGGTCGCCGCG | 17 | 49 |
| 46 | rpoB-R | ACGTGACAGACCGCCGGGC | 19 | 52 |

Example 1

Quantitative Asymmetric MTB PCR

Sample Processing

DNA from 25 μl of *M. tuberculosis* suspension was extracted using 100 μl of DNA Extraction Solution (Epicentre) according to the manufacturer protocol.

Five separate assays for amplification and detection of *M. tuberculosis* were developed. One primer in each assay was biotinylated. The probe used in each assay captures biotinylated amplicons generated by the biotinylated primer (see detection of amplicons, below).

TABLE 3

| Assay | Forward Primer | Reverse Primer | Probe | PCR Product (bases) |
|---|---|---|---|---|
| 1 | Bi-1-ponA-F (SEQ ID NO: 15) | 1-ponA-R (SEQ ID NO: 18) | 1-ponA-probe (SEQ ID NO: 30) | 270 |
| 2 | 2-ponA-F (SEQ ID NO: 17) | Bi-2-ponA-R (SEQ ID NO: 20) | 2-ponA-probe (SEQ ID NO: 31) | 205 |

TABLE 3-continued

| Assay | Forward Primer | Reverse Primer | Probe | PCR Product (bases) |
|---|---|---|---|---|
| 3 | 3-ponA-F (SEQ ID NO: 11) | Bi-3-ponA-R (SEQ ID NO: 14) | 3-ponA-probe (SEQ ID NO: 27) | 185 |
| 4 | Bi-1-ponA-F (SEQ ID NO: 15) | 1-ponA-R (SEQ ID NO: 18) | 1-ponA-probe-a (SEQ ID NO: 42) | 270 |
| 5 | 2-ponA-F (SEQ ID NO: 17) | Bi-2-ponA-R-a (SEQ ID NO: 36) | 2-ponA-probe-a (SEQ ID NO: 43) | 157 |

PCR Amplification

PCR was performed using HotStarTag PCR kit (Qiagen). Primers used in this study are directed towards target sequences in the ponA gene that exist only in pathogenic *Mycobacterium tuberculosis* (MTB complex), and are not generally found in the commensal *Mycobacterium* species or other bacteria. In this example, the primer and probe combinations of Assays 1-3 were used. One primer used in each assay was biotinylated at the 5' end and the other primer was not (Table 3). The PCR mixture contains 10 μl of the test sample DNA, 0.25 μl (0.625 pmoles) of unbiotinylated primer, 10 μl (25 pmoles) of biotinylated primer, 10 μl (0.25 mM) deoxynucleosides triphosphates (dNTPs), 4 μl (0.1 mM MgCl2), 10 μl of 10×PCR buffer (from Qiagen kit), 0.5 μl of QTaq (2.5 units—from Qiagen kit) and sterile water added to bring up the final volume to 100 μl. Cycling times were 90 sec at 95° C., followed by 50 cycles at 95° C. for 1 min, annealing temperature beginning at 61° C. and ending at 56° C. for 1 min, and 72° C. for 45 sec. The annealing temperature was lowered 0.1° C. every cycle until it reached 56° C.

This followed by 10 cycles at 95° C. for 1 min, annealing temperature beginning at 54° C. and ending at 54° C. for 1 min, and 72° C. for 45 sec. and 1 cycle at 72° C. for 1 sec at the end.

Colorimetric Detection of Amplified MTB ponA Gene

After amplification, PCR products were denatured with 10 μl of a solution (3.4% sodium hydroxide (NaOH) containing 100 mM disodium ethylenediamine tetraacetic acid (Na2EDTA pH10.0) in the reaction tubes prior to capture onto multi-well plate (Immulon II removawell, Dinex) coated with the probe.

To capture the biotinylated PCR product 100 ng of probe in 100 μl of 1M Ammonium acetate was adhered to the multi-well plate and incubated overnight at 37° C. Then the plate was washed with 175 μl of 2.5× sodium saline sulfate EDTA (SSPE) buffer (375 mM sodium chloride (NaCl), 2.5 mM sodium phosphate (NaH2PO4), 5 mM tetrasodium ethylenediamine tetraacetic acid (Na4EDTA), pH7.0 containing 0.08% sodium dodecyl sulfate (SDS)) and air dried for 3 hr. Plates can be stored in a sealed bag at 2-8° C. for up to 9 months. Then 175 μl of 8× sodium saline sulfate (SSP) buffer (1.5 M NaCl, 100 mM NaH2PO4, pH 4.0) hybridization buffer containing 8% formamide was added to each well followed by 100 μl of each denatured PCR product and mixed by gently pipetting up and down. Plates were incubated at 37° C. for 30 min and then washed with 2.5×SSPE buffer on a plate shaker. Hybridized biotinylated PCR products were detected by ExtrAvidin peroxidase (Sigma) diluted in 2.5×SSPE and tetramethyl benzidine dihydrochloride (TMB) (Sigma) substrate. The probe is complementary to amplicons containing the biotin label (positive result) but not to the biotinylated primer. Therefore biotinylated primer will not be captured onto a plate containing the probe (negative result).

Quantification

To calculate the colony forming units (CFU) from the quantitative PCR signal intensity, six to ten fold serial dilutions and a negative control were prepared by diluting genomic DNA from *M. tuberculosis* strain BCG ($5\times10^3$ CFU) with DNA extracted from urogenital secretions of a uninfected individual. PCR and colorimetric detection of these ten-fold serial-dilutions were done simultaneously with the test samples. The signal intensity obtained from these reference ten-fold dilutions of *M. tuberculosis* was used to construct a standard curve (signal intensity vs. CFU). The signal intensity obtained in a test specimen is converted to CFU using the standard curve included in each run.

Analytical Sensitivity

Figure 2:
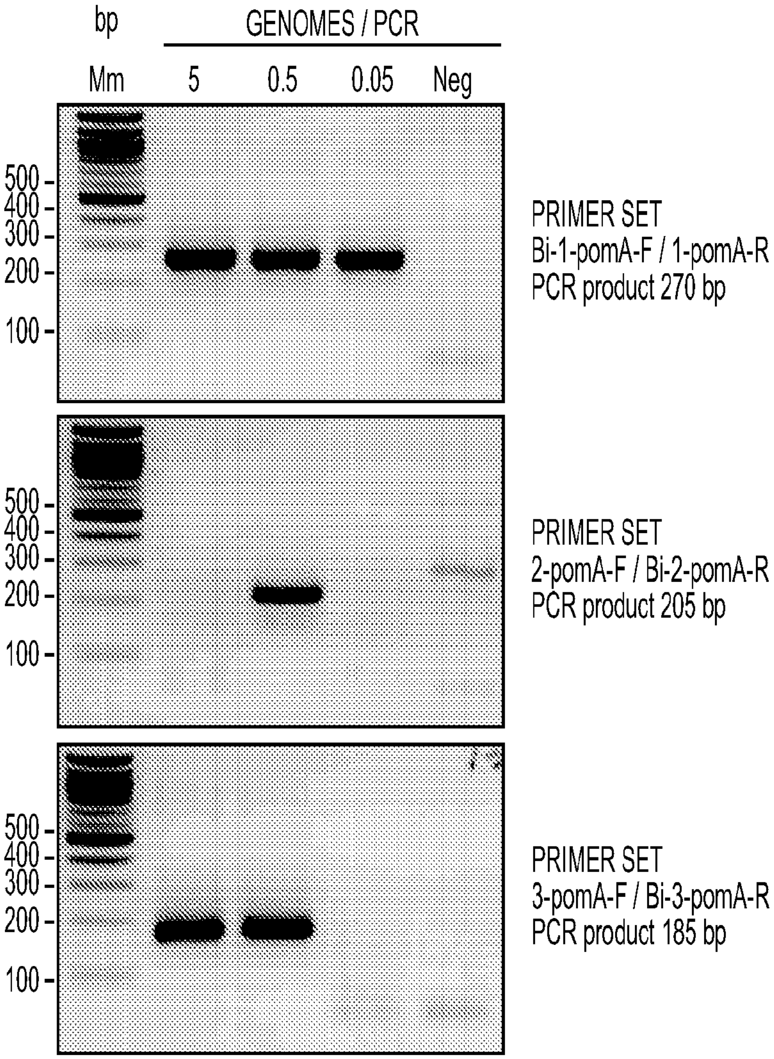
FIG. 2 shows gel images illustrating analytical sensitivity of *Mycobacterium tuberculosis* PCR with human specimen (vaginal swab from a healthy subject) using primer sets targeting the ponA gene. The upper panel utilized primers Bi-1-ponA-F (SEQ ID NO: 15) and 1-ponA-R (SEQ ID NO: 18). The middle panel utilized primers 2-ponA-F (SEQ ID NO: 17) and Bi-2-ponA-R (SEQ ID NO: 20). The lower panel utilized primers 3-ponA-F (SEQ ID NO: 11) and Bi-3-ponA-R (SEQ ID NO: 14). In all cases "Bi" indicates the primer that was labeled with Biotin.

The primers analytical sensitivity in human specimens was 0.05 to 0.5 *M. tuberculosis* genomes per PCR reaction equivalent to 20 to 200 bacteria per ml of clinical specimen (FIGS. 2 and 5). *M. tuberculosis* genomic DNA was serially diluted in human genomic DNA in equal amounts as in the negative control (about 0.5 to 2.5 μg/PCR).

Example 2

Xpert® MTB/RIF System Performance

Figure 5:
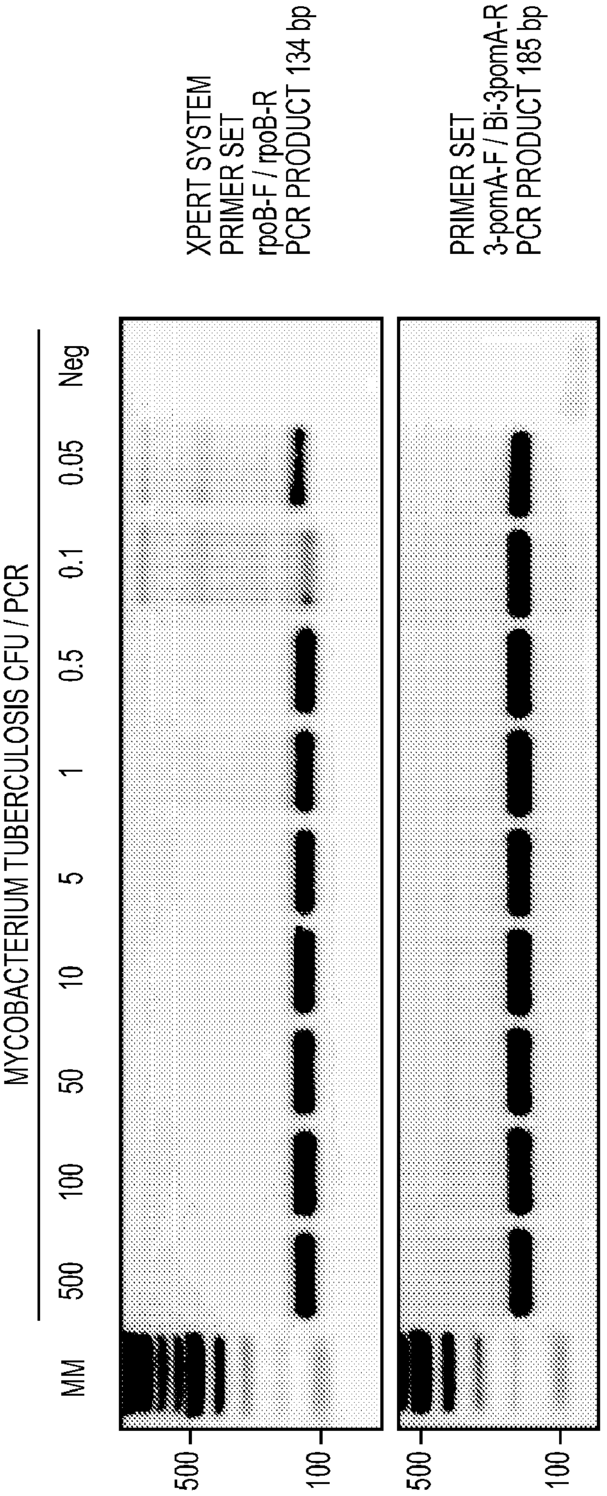
FIG. 5 shows gel images illustrating analytical sensitivity of *Mycobacterium tuberculosis* PCR in a human specimen (vaginal swab from a healthy subject) of primers 3-ponA-F (SEQ ID NO: 11) and Bi-3-ponA-R (SEQ ID NO: 14) compared side by side to the best primer set from current technology rpoB-F (SEQ ID NO: 45) and rpoB-R (SEQ ID NO: 46), which are the primers used in the included in the Xpert MTB/RIF system. This primer set was chosen for further evaluation because in certain ELISA format assays it gave a lower background and therefore is capable in certain contexts of a higher sensitivity.

The analysis was repeated with Xpert® MTB/RIF system probes rpoB-F and rpoB-R (Table 2C) according to procedures in Sample Processing and PCR Amplification described in Example 1 above, except that cycling times were 90 sec at 95° C., followed by 50 cycles at 95° C. for 1 min, annealing temperature beginning at 56° C. and ending at 51° C. for 1 min, and 72° C. for 45 sec. The annealing temperature was lowered 0.1° C. every cycle until it reached 51° C. This followed by 10 cycles at 95° C. for 1 min, annealing temperature beginning at 54° C. and ending at 54° C. for 1 min, and 72° C. for 45 sec. and 1 cycle at 72° C. for 1 sec at the end. In a head to head comparison, probes/primers of the current invention demonstrated superior performance (FIG. 5).

Example 3

Quantitative Asymmetric MTB PCR

Figure 4:
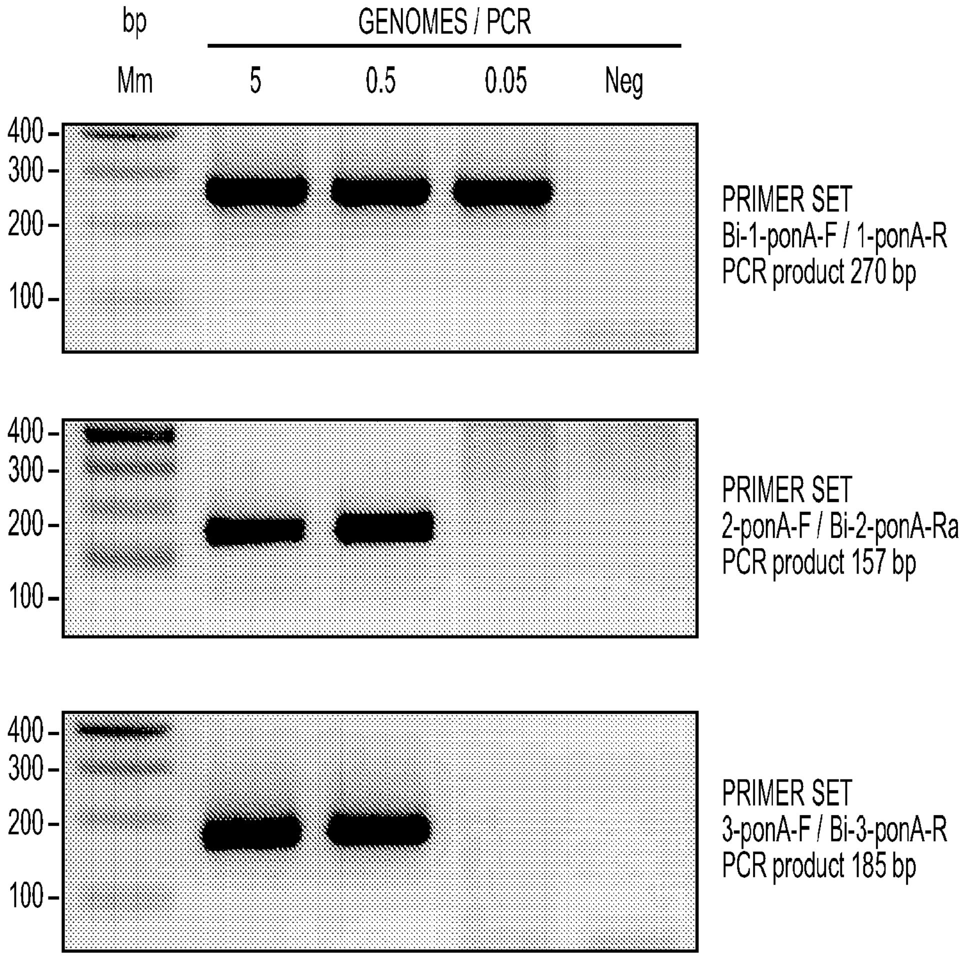
FIG. 4 shows gel images illustrating the analytical sensitivity of *Mycobacterium tuberculosis* PCR in a human specimen (vaginal swab from a healthy subject) with three primer sets targeting ponA gene. The upper panel utilized primers Bi-1-ponA-F (SEQ ID NO: 15) and 1-ponA-R (SEQ ID NO: 18). The middle panel utilized primers 2-ponA-F (SEQ ID NO: 17) and the alternative primer Bi-2-ponA-Ra (SEQ ID NO: 36). The lower panel utilized primers 3-ponA-F (SEQ ID NO: 11) and Bi-3-ponA-R (SEQ ID NO: 14). In all cases "Bi" indicates the primer that was labeled with Biotin.

This example was performed similarly to Example 1, except that assay 5 was substituted for assay 2. The primers analytical sensitivity in human specimens was 0.05 to 0.5 MTB genomes per PCR reaction equivalent to 20 to 200 bacteria per ml of clinical specimen (FIG. 4).

Example 4

Quantitative Asymmetric MTB PCR of Sputum Samples

Reagents

Buffer 1: Ascorbic Acid 0.1M, Hydrogen peroxide 4%, (pH4, stored at 4° C.).

Buffer 2: NaOH 0.1M, Thymol Blue 0.01%, (pH 10, Blue, stored at RT).

QuickExtract DNA Extraction Solution 1.0 (50 ml) Cat. No. QE09050 EPICENTRE Biotechnologies. Note: When the DNA extraction solution (50 ml) was received from EPICENTRE 10 ul of 2% Phenol RED was added, which turns it magenta-pink.

Procedure 200 ul of buffer 1 and glass beads were added to a sputum sample.

With heavy vortexing, a foamy white homogeneous suspension was obtained (blood turned brown-yellow). Heavily bloody sputa required 200 ul more of buffer 1.

200 ul of buffer 2 was added. With heavy vortexing a blue-green foamy solution was obtained. Very sticky samples remained yellow-green and needed 200 ul more of buffer 2.

In about 30 sec the sample separated into a liquid blue part (bottom) and a foamy green (upper) part, indicating successful digestion.

50 ul of the liquid blue part (with some glass bids desirable) was pipetted into 200 ul of EPICENTRE DNA extraction solution in a 1.5 ml screw-cap vial.

After the addition of the processed sputum, vortexing turned the DNA preparation purple-magenta indicating optimal pH (8 to 9). (Note that yellow-orange is not good (pH 5 to 7)).

DNA extraction involved three consecutive steps: 1) heating at 57° C. for 2 to 30 min; 2) then heating at 97° C. for 2 to 10 min; and 3) cooling at −20° C. for about 10 min.

Vortexing once before and once after each incubation was found to work best. Incubation times were found to not be crucial although incubation at 97° C. should never exceed 17 min.

At this point the DNA preparation was optionally stored at −80° C. If PCR was performed immediately after DNA extraction, a short (2 min) spin in a bench top centrifuge at 10,000 rpm was used to sediment any cell debris.

The assay 3 probe and primer combination was used on samples processed in this manner and compared to the Xpert® MTB/RIF system probes rpoB-F and rpoB-R (Table 2C) as described in Example 2. As shown in FIG. 6, the analytical sensitivity was 0.01 MTB genomes per PCR reaction. This result implies that at least 95% of the time this assay will detect the presence of a single *M. tuberculosis* cell in a sample.

Example 5

Detection of *M. tuberculosis* Infection in Clinical Patient Samples

Selection of Patients

The number of tuberculosis (TB) cases in Boston is relatively low (Boston Public Health Commission. Tuberculosis Impact in Boston Residents: 2012). Over the last 3 years (2010-2012), the number of cases (and the corresponding TB incidence rate per 100,000 population) has fluctuated from 58 (9.8) to 41 (6.6). Seventy percent of these patients have pulmonary TB, 80% are foreign born, and 6-8% are HIV co-infected. The majority (65-75%) of patients are diagnosed during an admission to a health facility (inpatient diagnosis). Also, 60% of patients are either sputum smear-negative/culture positive or smear-negative/culture-negative, considerably complicating the initial diagnosis of TB and often delaying the initiation of appropriate treatment.

The development of new TB cases is fueled by a large number of persons with latent TB infection (LTBI) that are at risk of developing active TB disease. In 2012, the Boston Public Health Commission (BPHC) evaluated 1,446 persons for LTBI, corresponding to an incidence rate of 240/100,000 in females and 205/100,000 in males.

Boston Medical Center (BMC)—the principal safety net hospital in the greater Boston area—is the epicenter of TB in Boston (Table 4). Every month, approximately 50 patients are tested for *M. tuberculosis* at the BMC microbiology laboratory (600 per year); and about 5% of these patients are found to have TB disease and reported to the BPHC each month. In fact, BMC regularly contributes ⅔ of all TB cases reported to BPHC each year; in 2011, BMC reported 66% (29/44) of TB cases, in 2012, 63% (26/41), and as of November 2013, 37 cases year to date. The monthly distribution of TB cases at BMC is constant with 0-5 (average 2.6) TB cases diagnosed per month (Table 4).

Table 4: Summary of TB patients diagnosed at Boston Medical Center (BMC) during 2011-2013 using existing diagnostic tests in respiratory specimens (sputum and bronchoalveolar lavages). Testing was done in patients suspected of having pulmonary TB (i.e. TB SUSPECTS).

TABLE 4

| | 2011 | 2012 | 2013* | Totals |
|---|---|---|---|---|
| Per patient analysis | | | | |
| Approximate number of patients tested for *M. tuberculosis* (pulmonary TB suspects) | 600 | 600 | 600 | 1,800 |
| Number of TB patients reported to BPHC (%) | 29 (4.8) | 26 (4.3) | 37 (6.2) | 96 (5.3) |
| Number of TB patients reported per month: | | | | |
| Range | 0-5 | 0-4 | 1-5 | 0-5 |
| Mean | 2.4 | 2.2 | 3.4 | 2.6 |

*(Jan-Nov 2013)

Analytical Sensitivity

To evaluate the analytical sensitivity of the ponA primer set in serial dilutions of *M. bovis* (BCG) genomic DNA in clinical specimens, ethical approvals to access discarded sputum specimens (n=146) from patients admitted to BMC during a 4-week period (Aug. 20 to Sep. 18, 2013) were obtained. Samples from TB suspects were excluded, as indicated by a laboratory request for TB testing (sputum smear microscopy and culture). The rheological characteristics of specimens adequately represented the variability seen in sputum from TB patients: low (<1 mL) volume (46%), blood content (32%), stickiness (29%), high (>15 mL) volume (24%), high saliva content (22%), and gelatinous (15%).

Before spiking the samples with BCG, they were tested with the assay primer and probe set in four sequential batches (Table 5) to ensure they were free of *M. tuberculosis* DNA. In an effort to minimize the possibility of cross-contamination, each batch was tested with new reagents and supplies on separate days. The presence of *M. tuberculosis* in positive samples (N=13) was confirmed by DNA sequencing as described below. The number of TB cases reported by BMC during the corresponding sampling window was 4 (August 2013) and 2 (September 2013).

Table 5: *M. tuberculosis* testing in discarded sputum samples of hospitalized patients with primer set 3ponA-F/R (assay 3) during a 4-week period at Boston Medical Center. Patients were not suspected of having pulmonary TB (i.e. NON-TB SUSPECTS).

TABLE 5

| | Batch 1 | Batch 2 | Batch 3 | Batch 4 | Totals |
|---|---|---|---|---|---|
| Number of samples tested | 42 | 32 | 43 | 29 | 146 |
| Number of samples positive for TB (%) | 2 (4.8) | 3 (9.4) | 5 (11.6) | 3 (10.3) | 13 (8.9) |
| *M. tuberculosis* genotypes | 1b, 2 | 1, 1, 2 | 0, 1, 1, 2, 2 | 1, 1, 4 | |

PonA Genotyping

The DNA amplicons targeted by primer/probe assays 1, 3, and 5 contain informative DNA sequences that distinguish *M. tuberculosis* form other Mycobacteria species. The amplicon targeted by assays 2 and 5 contains informative DNA sequences that distinguish: 1) All Mycobacteria species in the *M. tuberculosis* complex from each other, and 2) between strains of *Mycobacterium tuberculosis* isolated from a subject population. The amplicons could be sequenced by available commercial methods starting at both the 5' and 3' ends as appropriate.

Specimens detected positive with assay 3 were confirmed positive with assay 5 that targets a different region in the ponA gene that is sufficiently distant (~900 bp) to remain unaffected by amplicons generated while performing assay 3. Amplicons generated by assay 5, were sequenced and five possible genotypes: 0, 1, 2, 3, 4 and some variants such as "1 b" were identified. The genotype number denotes the number of consecutive proline codons (CCG or CCT) missing.

Discussion

The detection of *M. tuberculosis* in clinical samples by primer set 3ponA-F/R (assay 3) in patients with a low pre-test probability (non-TB suspects) is novel. The confirmatory results using a different primer set and the variability in ponA genotypes identified strongly suggest these results are not due to cross contamination, false-positive or artifactual.

Because the samples tested were anonymized and the clinical information of patients tested is unknown, the sensitivity or specificity of the assay cannot be estimated. However, based on the epidemiology of TB in Boston summarized above, the number of *M. tuberculosis* positive samples is well above what is expected. While high, this increased prevalence of TB is consistent with the high sensitivity of the PCR assay observed in spiked sputum specimens in the laboratory (level of detection of 0.01 genomes/PCR reaction).

These results, however, lead to a question: why are there not more cases of TB reported in the Boston area? Without wishing to be bound by theory the following reasoning may provide an explanation.

The intensity of the amplicon band separated by gel electrophoresis suggests the number of genome copies detected in the sputum samples is <10 genome/PCR reaction (below the level of detection of *M. tuberculosis* culture). Also, because all patients were hospitalized, samples were identified through a laboratory request for microbiological testing, and the sputum samples were grossly inflammatory (pus, blood, etc). Thus, it is likely that most patients had an underlying lung infection (i.e. pneumonia).

Considering these factors, it is possible the underlying primary infectious process may have reactivated dormant lung foci of *M. tuberculosis* with subsequent "spillage" of a small amount of *M. tuberculosis* genomes into sputum. If correct, it is conceivable that this process may not lead to clinical TB disease. Alternatively, the *M. tuberculosis* bacterial load is small enough and the antibiotics given as part of the primary treatment infectious process (i.e. pneumonia) are sufficient to abrogate the incipient development of TB disease. Although this is an extreme example, a similar explanation has been proposed in clinical trials seeking to "shorten TB treatment" by identifying patients early, at the time the bacterial load is reduced. Regardless of the underlying mechanism, the likely presence of such low levels of bacteria may have clinical significance.

Clinical Applications

The data presented suggests the sensitivity and specificity of the 3ponA-F/R primer set (assay 3) is unprecedented. Such a diagnostic assay opens the possibility of diagnosing patients earlier than currently possible with existing methods (including culture, which remains the reference method for *M. tuberculosis* diagnosis), including patients with paucibacillary TB disease such as: HIV-infected TB patients and other immunosuppressed states (post-transplant, immunosuppressive drugs such as chemotherapeutic drugs, steroids and TNF-alpha inhibitors); Children; and Contacts of patients with infectious TB (i.e. persons with LTBI) transitioning to active TB disease (e.g. early TB disease).

Thus, these primers and probes enable development of a diagnostic assay that can be used to screen patients for TB disease in a variety of clinical settings such as emergency rooms, outpatient and inpatient facilities, and community health clinics. Furthermore, the quantitative capabilities of the asymmetric assay may be useful for monitoring treatment response. The assay may be cost-effective to screen both TB suspects (where the prevalence is expected to be higher) as well as non-TB suspects (lower prevalence).

While the present teachings are described in conjunction with various embodiments, it is not intended that the present teachings be limited to such embodiments. On the contrary, the present teachings encompass various alternatives, modifications and equivalents, as will be appreciated by those of skill in the art. Thus, the invention as contemplated by applicants extends to all functionally equivalent structures, methods and uses, such as are within the scope of the appended claims.

Moreover, in the following claims it should be understood that the order of steps or order for performing certain actions (e.g. mixing of reactants) is immaterial so long as the present teachings remain operable. Unless expressly stated otherwise or where performing the steps of a claim in a certain order would be non-operative, the steps and/or substeps of the following claims can be executed in any order. Moreover, two or more steps or actions can be conducted simultaneously.

We claim:

1. At least one synthetic oligonucleotide that hybridizes to the Mycobacterium tuberculosis ponA gene, wherein the at least one synthetic oligonucleotide has a set of features selected from:

A) a calculated binding value in the range of 60 to 74 inclusive, wherein the nucleobase sequence of said synthetic oligonucleotide: (i) is selected to be from 23 to 27 nucleobase subunits in length; and (ii) possesses a nucleobase sequence that: 1) is identical in nucleobase sequence to a contiguous subsection of SEQ ID NO: 1; 2) is identical in nucleobase sequence to a contiguous subsection of SEQ ID NO: 1 except for the presence of one single point mutation as compared with SEQ ID NO: 1; 3) is identical in nucleobase sequence to a contiguous subsection of SEQ ID NO: 1 except for the presence of two point mutations as compared with SEQ ID NO: 1; or 4) is complementary to any one of 1) to 3);

B) a calculated binding value in the range of 52 to 66 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a contiguous subsection of SEQ ID NO: 4; 2) is identical in nucleobase sequence to a contiguous subsection of SEQ ID NO: 4 except for the presence of one single point mutation as compared with SEQ ID NO: 4; 3) is identical in nucleobase sequence to a contiguous subsection of SEQ ID NO: 4 except for the presence of two point mutations as compared with SEQ ID NO: 4; or 4) is complementary to any one of 1) to 3);

C) a calculated binding value in the range of 52 to 66 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a contiguous subsection of SEQ ID NO: 5; 2) is identical in nucleobase sequence to a contiguous subsection of SEQ ID NO: 5 except for the presence of one single point mutation as compared with SEQ ID NO: 5; 3) is identical in nucleobase sequence to a contiguous subsection of SEQ ID NO: 5 except for the presence of two point mutations as compared with SEQ ID NO: 5; or 4) is complementary to any one of 1) to 3);

D) a calculated binding value in the range of 51 to 65 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a contiguous subsection of SEQ ID NO: 8; 2) is identical in nucleobase sequence to a contiguous subsection of SEQ ID NO: 8 except for the presence of one single point mutation as compared with SEQ ID NO: 8; or 3) is identical in nucleobase sequence to a contiguous subsection of SEQ ID NO: 8except for the presence of two point mutations as compared with SEQ ID NO: 8; or 4) is complementary to any one of 1) to 3);

E) a calculated binding value in the range of 51 to 65 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a contiguous subsection of SEQ ID NO: 7; 2) is identical in nucleobase sequence to a contiguous subsection of SEQ ID NO: 7 except for the presence of one single point mutation as compared with SEQ ID NO: 7; or 3) is identical in nucleobase sequence to a contiguous subsection of SEQ ID NO: 7 except for the presence of two point mutations as compared with SEQ ID NO: 7; or 4) is complementary to any one of 1) to 3);

F) a calculated binding value in the range of 48 to 62 inclusive, wherein the nucleobase sequence of said synthetic oligonucleotide: (i) is selected to be from 18 to 21 nucleobase subunits in length; and (ii) possesses a nucleobase sequence that: 1) is identical in nucleobase sequence to a contiguous subsection of SEQ ID NO: 10; 2) is identical in nucleobase sequence to a contiguous subsection of SEQ ID NO: 10except for the presence of one single point mutation as compared with SEQ ID NO: 10 ; 3) is identical in nucleobase sequence to a contiguous subsection of SEQ ID NO: 10 except for the presence of two point mutations as compared with SEQ ID NO: 10; or 4) is complementary to any one of 1) to 3);

G) a calculated binding value in the range of 48 to 62 inclusive, wherein the nucleobase sequence of said synthetic oligonucleotide: (i) is selected to be from 18 to 21 nucleobase subunits in length; and (ii) possesses a nucleobase sequence that: 1) is identical in nucleobase sequence to a contiguous subsection of SEQ ID NO: 34 ; 2) is identical in nucleobase sequence to a contiguous subsection of SEQ ID NO: 34 except for the presence of one single point mutation as compared with SEQ ID NO: 34; 3) is identical in nucleobase sequence to a contiguous subsection of SEQ ID NO: 34 except for the presence of two point mutations as compared with SEQ ID NO: 34; or 4) is complementary to any one of 1) to 3);

H) a calculated binding value in the range of 55 to 69 inclusive, wherein the nucleobase sequence of said synthetic oligonucleotide: (i) is selected to be from 23 to 26 nucleobase subunits in length; and (ii) possesses a nucleobase sequence that: 1) is identical in nucleobase sequence to a contiguous subsection of SEQ ID NO: 21; 2) is identical in nucleobase sequence to a contiguous subsection of SEQ ID NO: 21 except for the presence of one single point mutation as compared with SEQ ID NO: 21; 3) is identical in nucleobase sequence to a contiguous subsection of SEQ ID NO: 21 except for the presence of two point mutations as compared with SEQ ID NO: 21; or 4) is complementary to any one of 1) to 3);

I) a calculated binding value in the range of 48 to 62 inclusive, wherein the nucleobase sequence of said synthetic oligonucleotide: (i) is selected to be from 20 to 23 nucleobase subunits in length; and (ii) possesses a nucleobase sequence that: 1) is identical in nucleobase sequence to a contiguous subsection of SEQ ID NO: 24; 2) is identical in nucleobase sequence to a contiguous subsection of SEQ ID NO: 24 except for the presence of one single point mutation as compared with SEQ ID NO: 24; 3) is identical in nucleobase sequence to a contiguous subsection of SEQ ID NO: 24 except for the presence of two point mutations as compared with SEQ ID NO: 24; or 4) is complementary to any one of 1) to 3);

J) a calculated binding value in the range of 52 to 66 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a contiguous subsection of SEQ ID NO: 25; 2) is identical in nucleobase sequence to a contiguous subsection of SEQ ID NO: 25 except for the presence of one single point mutation as compared with SEQ ID NO: 25; 3) is identical in nucleobase sequence to a contiguous subsection of SEQ ID NO: 25 except for the presence of two point mutations as compared with SEQ ID NO: 25; or 4) is complementary to any one of 1) to 3);

K) a calculated binding value in the range of 52 to 66 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a contiguous subsection of SEQ ID NO: 38; 2) is identical in nucleobase sequence to a contiguous subsection of SEQ ID NO: 38 except for the presence of one single point mutation as compared with SEQ ID NO: 38; 3) is identical in nucleobase sequence to a contiguous subsection of SEQ ID NO: 38 except for the presence of two point mutations as compared with SEQ ID NO: 38; or 4) is complementary to any one of 1) to 3); and L) a calculated binding value in the range of 52 to 66 inclusive, wherein the nucleobase sequence of said synthetic oligonucleotide: (i) is selected to be from 21 to 24 nucleobase subunits in length; and (ii) possesses a nucleobase sequence that: 1) is identical in nucleobase sequence to a contiguous subsection of SEQ ID NO: 39; 2) is identical in nucleobase sequence to a contiguous subsection of SEQ ID NO: 39 except for the presence of one single point mutation as compared with SEQ ID NO: 39; 3) is identical in nucleobase sequence to a contiguous subsection of SEQ ID NO: 39 except for the presence of two point mutations as compared with SEQ ID NO: 39; or 4) is complementary to any one of 1) to 3).

2. The synthetic oligonucleotide of claim 1, wherein the at least one synthetic oligonucleotide consists of the nucleobase sequence of SEQ ID NO: 11.

3. The synthetic oligonucleotide of claim 1, wherein the at least one synthetic oligonucleotide consists of the nucleobase sequence of SEQ ID NO: 14.

4. The synthetic oligonucleotide of claim 1, wherein the at least one synthetic oligonucleotide consists of the nucleobase sequence of SEQ ID NO: 15.

5. The synthetic oligonucleotide of claim 1, wherein the at least one synthetic oligonucleotide consists of the nucleobase sequence of SEQ ID NO: 18.

6. The synthetic oligonucleotide of claim 1, wherein the at least one synthetic oligonucleotide consists of the nucleobase sequence of SEQ ID NO: 17.

7. The synthetic oligonucleotide of claim 1, wherein the at least one synthetic oligonucleotide consists of the nucleobase sequence of SEQ ID NO: 20.

8. The synthetic oligonucleotide of claim 1, wherein the at least one synthetic oligonucleotide consists of the nucleobase sequence of SEQ ID NO: 36.

9. The synthetic oligonucleotide of claim 1, wherein the at least one synthetic oligonucleotide consists of the nucleobase sequence of SEQ ID NO: 27.

10. The synthetic oligonucleotide of claim 1, wherein the at least one synthetic oligonucleotide consists of the nucleobase sequence of SEQ ID NO: 30.

11. The synthetic oligonucleotide of claim 1, wherein the at least one synthetic oligonucleotide consists of the nucleobase sequence of SEQ ID NO: 31.

12. The synthetic oligonucleotide of claim 1, wherein the at least one synthetic oligonucleotide consists of the nucleobase sequence of SEQ ID NO: 42.

13. The synthetic oligonucleotide of claim 1, wherein the at least one synthetic oligonucleotide consists of the nucleobase sequence of SEQ ID NO: 43.

14. The synthetic oligonucleotide of claim 1, wherein the at least one synthetic oligonucleotide comprises a label.

* * * * *